US009951299B2

(12) United States Patent
De Maria et al.

(10) Patent No.: US 9,951,299 B2
(45) Date of Patent: Apr. 24, 2018

(54) CUTINASE VARIANTS AND POLYNUCLEOTIDES ENCODING SAME

(71) Applicant: Novozymes A/S, Bagsvaerd (DK)

(72) Inventors: Leonardo De Maria, Frederiksberg (DK); Rakhi Saikia, Bangalore (IN); Santhosh Vasu Mepadam, Bangalore (IN); Ting Sun, Beijing (CN)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 15/101,275

(22) PCT Filed: Dec. 10, 2014

(86) PCT No.: PCT/CN2014/093438
§ 371 (c)(1),
(2) Date: Jun. 2, 2016

(87) PCT Pub. No.: WO2015/085920
PCT Pub. Date: Jun. 18, 2015

(65) Prior Publication Data
US 2016/0355759 A1    Dec. 8, 2016

(30) Foreign Application Priority Data

Dec. 11, 2013  (WO) ................ PCT/CN2013/089115

(51) Int. Cl.
*C12N 9/18* (2006.01)
*C11D 3/386* (2006.01)
*C11D 11/00* (2006.01)
*D06M 16/00* (2006.01)
*D06M 101/32* (2006.01)

(52) U.S. Cl.
CPC ...... *C11D 3/38636* (2013.01); *C11D 11/0017* (2013.01); *C12N 9/18* (2013.01); *C12Y 301/01074* (2013.01); *D06M 16/003* (2013.01); *D06M 2101/32* (2013.01); *D06M 2200/35* (2013.01)

(58) Field of Classification Search
CPC .......................... C12N 9/15; C12Y 301/01074
See application file for complete search history.

(56) References Cited

U.S. PATENT DOCUMENTS

2011/0137002 A1*  6/2011  Hauer ..................... C12N 9/16
526/328

FOREIGN PATENT DOCUMENTS

| WO | 1994014963 A1 | 7/1994 |
| WO | 1995022615 A1 | 8/1995 |
| WO | 199727237 A1 | 7/1997 |
| WO | 199901604 A1 | 1/1999 |
| WO | 200034450 A1 | 6/2000 |
| WO | 200134899 A1 | 5/2001 |
| WO | 200192502 A1 | 12/2001 |
| WO | 2003076580 A2 | 9/2003 |
| WO | 2006111163 A1 | 10/2006 |
| WO | 2013171072 A1 | 11/2013 |

OTHER PUBLICATIONS

Ogino et al. 2007; Standard mutation nomenclature in molecular diagnostics. Practical and educational challenges. J. Molecular Diagnostics 9(1):1-6.*
Baker et al, 2011, Appl Microbiol Biotechnol 93(1), 229-240.

* cited by examiner

*Primary Examiner* — Karen Cochrane Carlson
(74) *Attorney, Agent, or Firm* — Eric J. Fechter

(57) ABSTRACT

The present invention relates to variants with cutinase activity of a parent cutinase, comprising an alteration at one or more (e.g. several) positions corresponding to positions: 36, 37, 40, 78, 90, 114, 150, 196, 216, or 217 of SEQ ID NO: 2, wherein the alteration is a substitution for positions 40, 78, 90, 114, 150, 196 and 216, and a deletion for positions 36, 37 and 217, and wherein the variant has at least 75% but less than 100% sequence identity to the mature polypeptide of SEQ ID NO: 2.
The present invention also relates to polynucleotides encoding the variants; nucleic acid constructs, vectors, and host cells comprising the polynucleotides; and method for obtaining and methods of producing the variants. It also relates to compositions comprising the variant, and to methods for using the variant.

19 Claims, No Drawings

SEQUENCE LISTING

```
<160> NUMBER OF SEQ ID NOS: 16

<210> SEQ ID NO 1
<211> LENGTH: 687
<212> TYPE: DNA
<213> ORGANISM: Artificial sequence
<220> FEATURE:
<223> OTHER INFORMATION: Synthetic Construct
<220> FEATURE:
<221> NAME/KEY: CDS
<222> LOCATION: (1)..(687)

<400> SEQUENCE: 1 atg aag ttc ttc acc acg atc ctc tcg act gcc tcg ttg gtc gca gcc     48
Met Lys Phe Phe Thr Thr Ile Leu Ser Thr Ala Ser Leu Val Ala Ala
1               5                   10                  15
```

| | | | | | | | | | | | | | | | | |
|---|---|---|---|---|---|---|---|---|---|---|---|---|---|---|---|---|
| ttg | cct | gcg | gca | gtg | gat | tcc | aac | cac | aca | ccg | gca | gca | ccc | gag | ctc | 96 |
| Leu | Pro | Ala | Ala | Val | Asp | Ser | Asn | His | Thr | Pro | Ala | Ala | Pro | Glu | Leu | |
| | | | 20 | | | | 25 | | | | | 30 | | | | |
| gtg | gca | cgc | cag | ctc | gga | gcc | atc | cag | aac | gac | ttg | gaa | tcg | ggt | tcg | 144 |
| Val | Ala | Arg | Gln | Leu | Gly | Ala | Ile | Gln | Asn | Asp | Leu | Glu | Ser | Gly | Ser | |
| | | 35 | | | | | 40 | | | | | 45 | | | | |
| cct | gac | gcg | tgt | ccc | gat | gca | att | ctc | att | ttc | gca | cga | gga | tcg | atg | 192 |
| Pro | Asp | Ala | Cys | Pro | Asp | Ala | Ile | Leu | Ile | Phe | Ala | Arg | Gly | Ser | Met | |
| | 50 | | | | | 55 | | | | | 60 | | | | | |
| gaa | ccc | ggt | aac | atg | ggt | atc | act | gtc | gga | cct | gcg | ttg | gca | aac | ggt | 240 |
| Glu | Pro | Gly | Asn | Met | Gly | Ile | Thr | Val | Gly | Pro | Ala | Leu | Ala | Asn | Gly | |
| 65 | | | | | 70 | | | | | 75 | | | | | 80 | |
| ttg | aag | gag | cat | atc | ccc | aac | atc | tgg | att | cag | gga | gtg | ggt | ggc | cct | 288 |
| Leu | Lys | Glu | His | Ile | Pro | Asn | Ile | Trp | Ile | Gln | Gly | Val | Gly | Gly | Pro | |
| | | | | 85 | | | | | 90 | | | | | 95 | | |
| tac | gac | gca | gcg | ctc | gca | acc | aac | ttc | ttg | cct | cgc | gga | acg | tcg | cag | 336 |
| Tyr | Asp | Ala | Ala | Leu | Ala | Thr | Asn | Phe | Leu | Pro | Arg | Gly | Thr | Ser | Gln | |
| | | | 100 | | | | | 105 | | | | | 110 | | | |
| gcc | aac | atc | gac | gag | gga | aaa | agg | ctc | ttc | cac | ctc | gcc | cat | cag | aag | 384 |
| Ala | Asn | Ile | Asp | Glu | Gly | Lys | Arg | Leu | Phe | His | Leu | Ala | His | Gln | Lys | |
| | | 115 | | | | | 120 | | | | | 125 | | | | |
| tgt | ccc | aac | aca | ccg | gtg | gtg | gca | gga | gga | tac | tcc | cag | ggt | gca | gcg | 432 |
| Cys | Pro | Asn | Thr | Pro | Val | Val | Ala | Gly | Gly | Tyr | Ser | Gln | Gly | Ala | Ala | |
| | 130 | | | | | 135 | | | | | 140 | | | | | |
| ttg | att | gcc | gca | gcc | gtc | tcg | gaa | ttg | tcg | gga | gca | gtg | aag | gag | cag | 480 |
| Leu | Ile | Ala | Ala | Ala | Val | Ser | Glu | Leu | Ser | Gly | Ala | Val | Lys | Glu | Gln | |
| 145 | | | | | 150 | | | | | 155 | | | | | 160 | |
| gtc | aag | gga | gtc | gtc | ttg | ttc | gga | tac | acc | cag | aac | ctc | cag | aac | cga | 528 |
| Val | Lys | Gly | Val | Val | Leu | Phe | Gly | Tyr | Thr | Gln | Asn | Leu | Gln | Asn | Arg | |
| | | | | 165 | | | | | 170 | | | | | 175 | | |
| gga | ggc | att | ccc | aac | tat | cct | cgc | gag | cgc | acg | aag | gtg | ttc | tgt | aac | 576 |
| Gly | Gly | Ile | Pro | Asn | Tyr | Pro | Arg | Glu | Arg | Thr | Lys | Val | Phe | Cys | Asn | |
| | | | 180 | | | | | 185 | | | | | 190 | | | |
| gtg | ggt | gat | gcc | gtg | tgt | aca | ggc | atc | ccg | atc | atc | act | cct | gcc | cac | 624 |
| Val | Gly | Asp | Ala | Val | Cys | Thr | Gly | Ile | Pro | Ile | Ile | Thr | Pro | Ala | His | |
| | | 195 | | | | | 200 | | | | | 205 | | | | |
| ctc | tcg | tat | acc | atc | cag | gcg | agg | ggt | gag | gca | gca | cgg | ttc | ctc | gtc | 672 |
| Leu | Ser | Tyr | Thr | Ile | Gln | Ala | Arg | Gly | Glu | Ala | Ala | Arg | Phe | Leu | Val | |
| | 210 | | | | | 215 | | | | | 220 | | | | | |
| gac | cga | att | agg | gcg | | | | | | | | | | | | 687 |
| Asp | Arg | Ile | Arg | Ala | | | | | | | | | | | | |
| 225 | | | | | | | | | | | | | | | | |

<210> SEQ ID NO 2
<211> LENGTH: 229
<212> TYPE: PRT
<213> ORGANISM: Artificial sequence
<220> FEATURE:
<223> OTHER INFORMATION: Synthetic Construct

<400> SEQUENCE: 2

Met Lys Phe Phe Thr Thr Ile Leu Ser Thr Ala Ser Leu Val Ala Ala
1               5                   10                  15

Leu Pro Ala Ala Val Asp Ser Asn His Thr Pro Ala Ala Pro Glu Leu
            20                  25                  30

Val Ala Arg Gln Leu Gly Ala Ile Gln Asn Asp Leu Glu Ser Gly Ser
        35                  40                  45

Pro Asp Ala Cys Pro Asp Ala Ile Leu Ile Phe Ala Arg Gly Ser Met
    50                  55                  60

Glu Pro Gly Asn Met Gly Ile Thr Val Gly Pro Ala Leu Ala Asn Gly

```
                65                  70                  75                  80
Leu Lys Glu His Ile Pro Asn Ile Trp Ile Gln Gly Val Gly Pro
                    85                  90                  95
Tyr Asp Ala Ala Leu Ala Thr Asn Phe Leu Pro Arg Gly Thr Ser Gln
                100                 105                 110
Ala Asn Ile Asp Glu Gly Lys Arg Leu Phe His Leu Ala His Gln Lys
                115                 120                 125
Cys Pro Asn Thr Pro Val Val Ala Gly Gly Tyr Ser Gln Gly Ala Ala
            130                 135                 140
Leu Ile Ala Ala Ala Val Ser Glu Leu Ser Gly Ala Val Lys Glu Gln
145                 150                 155                 160
Val Lys Gly Val Val Leu Phe Gly Tyr Thr Gln Asn Leu Gln Asn Arg
                165                 170                 175
Gly Gly Ile Pro Asn Tyr Pro Arg Glu Arg Thr Lys Val Phe Cys Asn
                180                 185                 190
Val Gly Asp Ala Val Cys Thr Gly Ile Pro Ile Ile Thr Pro Ala His
            195                 200                 205
Leu Ser Tyr Thr Ile Gln Ala Arg Gly Glu Ala Ala Arg Phe Leu Val
            210                 215                 220
Asp Arg Ile Arg Ala
225

<210> SEQ ID NO 3
<211> LENGTH: 17
<212> TYPE: PRT
<213> ORGANISM: Artificial Sequence
<220> FEATURE:
<223> OTHER INFORMATION: ARTIFICIAL PRIMER

<400> SEQUENCE: 3

Ala Ala Val Asp Ser Asn His Thr Pro Ala Val Pro Glu Leu Val Ala
1               5                   10                  15
Arg

<210> SEQ ID NO 4
<211> LENGTH: 16
<212> TYPE: PRT
<213> ORGANISM: Artificial Sequence
<220> FEATURE:
<223> OTHER INFORMATION: ARTIFICIAL PRIMER

<400> SEQUENCE: 4

Ala Val Asp Ser Asn His Thr Pro Ala Val Pro Glu Leu Val Ala Arg
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: ARTIFICIAL PRIMER

<400> SEQUENCE: 5

Val Asp Ser Asn His Thr Pro Ala Val Pro Glu Leu Val Ala Arg
1               5                   10                  15

<210> SEQ ID NO 6
<211> LENGTH: 14
<212> TYPE: PRT
<213> ORGANISM: Artificial Sequence
<220> FEATURE:
```

<223> OTHER INFORMATION: ARTIFICIAL PRIMER

<400> SEQUENCE: 6

Asp Ser Asn His Thr Pro Ala Val Pro Glu Leu Val Ala Arg
1               5                   10

<210> SEQ ID NO 7
<211> LENGTH: 13
<212> TYPE: PRT
<213> ORGANISM: Artificial Sequence
<220> FEATURE:
<223> OTHER INFORMATION: ARTIFICIAL PRIMER

<400> SEQUENCE: 7

Ser Asn His Thr Pro Ala Val Pro Glu Leu Val Ala Arg
1               5                   10

<210> SEQ ID NO 8
<211> LENGTH: 12
<212> TYPE: PRT
<213> ORGANISM: Artificial Sequence
<220> FEATURE:
<223> OTHER INFORMATION: ARTIFICIAL PRIMER

<400> SEQUENCE: 8

Asn His Thr Pro Ala Val Pro Glu Leu Val Ala Arg
1               5                   10

<210> SEQ ID NO 9
<211> LENGTH: 11
<212> TYPE: PRT
<213> ORGANISM: Artificial Sequence
<220> FEATURE:
<223> OTHER INFORMATION: ARTIFICIAL PRIMER

<400> SEQUENCE: 9

His Thr Pro Ala Val Pro Glu Leu Val Ala Arg
1               5                   10

<210> SEQ ID NO 10
<211> LENGTH: 10
<212> TYPE: PRT
<213> ORGANISM: Artificial Sequence
<220> FEATURE:
<223> OTHER INFORMATION: ARTIFICIAL PRIMER

<400> SEQUENCE: 10

Thr Pro Ala Val Pro Glu Leu Val Ala Arg
1               5                   10

<210> SEQ ID NO 11
<211> LENGTH: 9
<212> TYPE: PRT
<213> ORGANISM: Artificial Sequence
<220> FEATURE:
<223> OTHER INFORMATION: ARTIFICIAL PRIMER

<400> SEQUENCE: 11

Pro Ala Val Pro Glu Leu Val Ala Arg
1               5

<210> SEQ ID NO 12
<211> LENGTH: 8
<212> TYPE: PRT
<213> ORGANISM: Artificial Sequence
<220> FEATURE:
<223> OTHER INFORMATION: ARTIFICIAL PRIMER

```
<400> SEQUENCE: 12

Ala Val Pro Glu Leu Val Ala Arg
1               5

<210> SEQ ID NO 13
<211> LENGTH: 7
<212> TYPE: PRT
<213> ORGANISM: Artificial Sequence
<220> FEATURE:
<223> OTHER INFORMATION: ARTIFICIAL PRIMER

<400> SEQUENCE: 13

Val Pro Glu Leu Val Ala Arg
1               5

<210> SEQ ID NO 14
<211> LENGTH: 6
<212> TYPE: PRT
<213> ORGANISM: Artificial Sequence
<220> FEATURE:
<223> OTHER INFORMATION: ARTIFICIAL PRIMER

<400> SEQUENCE: 14

Pro Glu Leu Val Ala Arg
1               5

<210> SEQ ID NO 15
<211> LENGTH: 5
<212> TYPE: PRT
<213> ORGANISM: Artificial Sequence
<220> FEATURE:
<223> OTHER INFORMATION: ARTIFICIAL PRIMER

<400> SEQUENCE: 15

Glu Leu Val Ala Arg
1               5

<210> SEQ ID NO 16
<211> LENGTH: 4
<212> TYPE: PRT
<213> ORGANISM: Artificial Sequence
<220> FEATURE:
<223> OTHER INFORMATION: ARTIFICIAL PRIMER

<400> SEQUENCE: 16

Leu Val Ala Arg
1
```

CUTINASE VARIANTS AND POLYNUCLEOTIDES ENCODING SAME

CROSS-REFERENCE TO RELATED

This application is a 35 U.S.C. 371 national application of PCT/CN2014/093438 filed Dec. 10, 2014, which claims priority or the benefit under 35 U.S.C. 119 of Chinese PCT application no. PCT/CN2013/089115 filed Dec. 11, 2013 the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to cutinase variants, polynucleotides encoding the variants, methods of producing the variants, and methods of using the variants.

Description of the Related Art

Poly(ethylene terephthalate) abbreviated as PET fibers accounts for the main part of the polyester applied by the textile industry. The fibers are produced by e.g. polycondensation of terephthalic acid and ethylene glycol, and drawing of fibers from a melt.

Polyester has certain key advantages including high strength, soft hand, stretch resistance, stain resistance, machine washability, wrinkle resistance and abrasion resistance. However, polyester is not so optimal in terms of its hydrophobicity, pilling, static, dyeability, inactive surface as a medium for adhering, i.e., softening or wettability enhancing compounds, lack of breathability and undesirable high shine or luster appearance.

Because of its strength, polyester fabrics and/or garments are subject to pill formation, and possibly the most important of the cloth finishing processes applied to polyester staple-fibre materials are those designed for control of pilling. All staple-fibre materials tend to form small balls or "pills" of entangled fibres at the cloth surface, when subjected to mild abrasion during wash and wear. If the fabric contains a substantial proportion of fibres having high resistance to flexural abrasion, the pills may be retained on the surface of the cloth in sufficient numbers to produce an unpleasant handle and appearance.

Another problem with polyester is that during synthesis of PET, cyclic or linear oligomers of poly (ethylene terephthalate), such as terephtalic acid-bis-2-benzoyloxy-ethylesther (BETEB) and/or cyclic tri(ethylene terephthalate) are formed. These oligomers are partly deposited on machinery and partly staying on/in the fibers. Oligomers tend to give fabrics a grayish appearance. This is due to deposits of oligomers on the surface of the fabric, which is particularly outspoken after high temperature wet processes like high temperature dyeing. The oligomers can be removed by severe alkaline treatment, which results in a significant loss of fiber material. Organic extraction of the oligomers is a technical possibility, but not industrially feasible.

The industry has made great efforts to improve the characteristics of polyester, amongst other by way of applying cutinases.

Cutinases are known from various fungi, such as a filamentous fungal cutinase, e.g. native to a strain of *Humicola* or *Fusarium*, specifically *H. insolens* such as e.g. *H. insolens* strain DSM1800 (U.S. Pat. No. 5,827,719), or *F. solani pisi*. Methods of reducing the pilling propensity of polyester fabrics and/or garments with a terephtalic acid diethyl ester hydrolytic enzyme (ETE hydrolytic enzyme) and/or an ethyleneglycol dibenzyl ester hydrolytic enzyme (BEB hydrolytic enzyme) (WO99/001604), methods for modifying polyester comprising treating polyester with a polyesterase enzyme (WO2001/34899), and enzymatic hydrolysis of cyclic oligomers of poly(ethylene terephthalate), which comprises subjecting the cyclic oligomer to the action of one or more carboxylic ester hydrolases (WO97/27237) have been disclosed.

Cutinase variants have been described such as in WO0192502 wherein *H. insolens* variants have been disclosed for the treatment of polyester textile.

However, there is continuously a need for improved benefit of enzymatic polyester fabric and/or garment treatment, including enhancing the efficiency of the enzymes to their substrates. Thus identification of such enzymes with improved properties for use in methods for treating fabrics would be desirable.

SUMMARY OF THE INVENTION

The present invention relates to variants with cutinase activity of a parent cutinase, comprising an alteration at one or more (e.g. several) positions corresponding to positions: 36, 37, 40, 78, 90, 114, 150, 196, 216, or 217 of SEQ ID NO: 2, wherein the alteration is a substitution for positions 40, 78, 90, 114, 150, 196 and 216, and a deletion for positions 36, 37 and 217, and wherein the variant has at least 75%, at least 80%, at least 85%, at least 90%, at least 95%, at least 96%, at least 97%, at least 98%, or at least 99%, but less than 100% sequence identity to the mature polypeptide of SEQ ID NO: 2.

The present invention also relates to polynucleotides encoding the variants; nucleic acid constructs, vectors, and host cells comprising the polynucleotides; and method for obtaining and methods of producing the variants.

The present invention furthermore relates to compositions comprising the variant, and relates to methods for modifying polyester comprising use of the variant; methods for hydrolyzing cyclic oligomers of poly(ethylene terephthalate comprising use of the variant; and methods for reducing the pilling propensity of fabrics comprising or consisting of polyester using the variant.

Definitions

Cutinase: The term "Cutinase" means a lipolytic enzyme with cutinase activity (EC3.1.1.74) that catalyzes the reaction: Cutin+$H_2O \rightleftharpoons$ Cutin monomers. For purposes of the present invention, cutinase activity is determined as described in example 3 using oligomer Terephtalic acid-bis-2-benzoyloxy-ethylesther (BETEB) as substrate. BETEB is a by-product during the PET synthesis and is generally remained in the fabric or garment during textile manufacturing. BETEB is produced by e.g. condensation of terephthalic acid, benzoic acid and ethylene glycol, which has the same unit of benzoyloxy-ethylester as PET.

In one aspect, the variants of the present invention have at least 20%, e.g., at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the cutinase activity of the mature polypeptide of SEQ ID NO: 2.

In some embodiments, the cutinase can be variants comprising a substitution and/or a deletion of one or more (e.g. several) amino acids of SEQ ID NO: 2. Preferably, the total number of amino acid substitutions, deletions and/or insertions of the SEQ ID NO: 2 is 1-20, e.g., 1-10 or 1-5, such as 1, 2, 3, 4, 5, 6, 7, 8, 9, 10, 11, 12, 13, 14, 15, 16, 17, 18, 19, or 20.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g., several) amino acids absent from the amino and/or carboxyl terminus of a mature polypeptide; wherein the fragment has cutinase activity. In one aspect, a fragment consists or comprises at least 172 amino acid residues (e.g., corresponding to amino acids 52 to 223 of SEQ ID NO: 2). In one aspect, a fragment comprises at least 80%, at least 85%, at least 90%, at least 91%, at least 92%, at least 93%, at least 94%, at least 95%, at least 96%, at least 97%, at least 98%, or at least 99%, but less than 100% of the number of amino acids of SEQ ID NO: 2. In one aspect, a fragment comprises at least 172 amino acid residues (e.g., amino acids 52 to 223 of SEQ ID NO: 2) and at least 80%, at least 85%, at least 90%, at least 91%, at least 92%, at least 93%, at least 94%, at least 95%, at least 96%, at least 97%, at least 98%, or at least 99%, but less than 100% of the number of amino acids of SEQ ID NO: 2.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such improved properties include, but are not limited to specific activity, substrate cleavage, substrate specificity, thermostability, and decreased pilling propensity.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 36 to 229 of SEQ ID NO: 2, amino acids 1 to 23 of SEQ ID NO: 2 are a signal-peptide, and amino acids 24 to 35 of SEQ ID NO: 2 are a pro-peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having cutinase activity. In one aspect, the mature polypeptide coding sequence is nucleotides 106 to 687 of SEQ ID NO: 1. Nucleotides 1 to 69 of SEQ ID NO: 1 encode a signal-peptide. Nucleotides 70 to 105 of SEQ ID NO: 1 encode a pro-peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent cutinase: The term "parent" or "parent cutinase" means a cutinase to which an alteration is made to produce the enzyme variants of the present invention. The parent may be a naturally occurring (wild-type) polypeptide or a variant or fragment thereof.

Polyester Textile: "Polyester" as used herein means a linear polymeric molecule containing in-chain ester groups and which are derived from the condensation of a diacid with a diol or from the polymerization of hydroxy acids. The present invention applies to both aliphatic and aromatic polyesters. However, particularly preferred are aromatic polyester articles which are used to produce fiber and resin and that comprise a synthetically produced long chain polymer comprising at least 85%, preferably at least 90% and most preferably at least 95%, by weight of an ester of a substituted aromatic carboxylic acid, such as substituted terephthalic acid or parasubstituted hydroxybenzoate. Other useful polyester articles include those made of bulk polymer, yarns, fabrics, films, resins and powders. The principal polyesters in industrial usage include polyethylene terephthalate (PET), tetramethylene terephthalate (PTMT), polybutylene terphthalate (PBT), polytrimethylene terephthalate (PTT) and polyethylenenaphthalate (PEN), polycyclohexanedimethylene terephthalate (CHDMT), poly (ethylene-4-oxybenzoate) A-Tell, polyglycolide, PHBA and 2GN. However, PET is the most common linear polymer produced and accounts for a majority of the polyester applied in industry today.

The polyester textile used herein is meant to include fibers, yarns, fabrics and garments comprising polyester. The polyester yarn or fabric or garment may be any yarn or fabric or garment that is made from pure poly (ethylene terephthalate), or that is made from blends of poly (ethylene terephthalate) fibers and any other material conventionally used for making textile.

In one aspect the polyester fabric is a fabric blend comprising at least 5% (w/w) of polyester, such as at least 10%, at least 20%, at least 30%, at least 40%, at least 50%, at least 55%, at least 60%, at least 65%, at least 70%, at least 75%, at least 80%, at least 85%, at least 90%, or at least 95% of polyester. In one aspect, the process of the invention is applied to fabrics or garments consisting essentially of poly(ethylene terephthalate) polyester material, i.e. pure poly(ethylene terephthalate) polyester material.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment–
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment–Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having cutinase activity. In one aspect, a subsequence consists or comprises at least 516 nucleotides (e.g., nucleotides 154 to 669 of SEQ ID NO: 1). In one aspect, a subsequence comprises at least 80%, at least 85%, at least 90%, at least 91%, at least 92%, at least 93%, at least 94%, at least 95%, at least 96%, at least 97%, at least 98%, or at least 99%, but less than 100% of the number of nucleotides of SEQ ID No: 1. In one aspect, a fragment comprises at least 516 nucleotides (e.g., nucleotides 154 to 669 of SEQ ID NO: 1) and at least 80%, at least 85%, at least 90%, at least 91%, at least 92%, at least 93%, at least 94%, at least 95%, at least 96%, at least 97%, at least 98%, or at least 99%, but less than 100% of the number of nucleotides of SEQ ID NO: 1.

Variant: The term "variant" means a polypeptide having cutinase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 20%, at least 30%, at least 40%, at least 50%, at least 55%, at least 60%, at least 65%, t least 70%, at least 75%, at least 80%, at least 85%, at least 90%, at least 95%, or at least 100% of the cutinase activity of the mature polypeptide of SEQ ID NO: 2.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Wild-type cutinase: The term "wild-type" cutinase means a cutinase expressed by a naturally occurring microorganism, such as a bacterium, yeast, or filamentous fungus found in nature.

Conventions for Designation of Variants

For purposes of the present invention, the mature polypeptide disclosed in SEQ ID NO: 2 is used to determine the corresponding amino acid residue in another cutinase. The amino acid sequence of another cutinase is aligned with the mature polypeptide disclosed in SEQ ID NO: 2, and based on the alignment, the amino acid position number corresponding to any amino acid residue in the mature polypeptide disclosed in SEQ ID NO: 2 is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another cutinase can be determined by an alignment of multiple polypeptide sequences using several computer programs including, but not limited to, MUSCLE (multiple sequence comparison by log-expectation; version 3.5 or later; Edgar, 2004, Nucleic Acids Research 32: 1792-1797), MAFFT (version 6.857 or later; Katoh and Kuma, 2002, Nucleic Acids Research 30: 3059-3066; Katoh et al., 2005, Nucleic Acids Research 33: 511-518; Katoh and Toh, 2007, Bioinformatics 23: 372-374; Katoh et al., 2009, Methods in Molecular Biology 537: 39-64; Katoh and Toh, 2010, Bioinformatics 26: 1899-1900), and EMBOSS EMMA employing ClustalW (1.83 or later; Thompson et al., 1994, Nucleic Acids Research 22: 4673-4680), using their respective default parameters.

When the other enzyme has diverged from the mature polypeptide of SEQ ID NO: 2 such that traditional sequence-based comparison fails to detect their relationship (Lindahl and Elofsson, 2000, J. Mol. Biol. 295: 613-615), other pairwise sequence comparison algorithms can be used.

Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, Nucleic Acids Res. 25: 3389-3402). Even greater sensitivity can be achieved if the family or superfamily for the polypeptide has one or more representatives in the protein structure databases. Programs such as GenTHREADER (Jones, 1999, J. Mol. Biol. 287: 797-815; McGuffin and Jones, 2003, Bioinformatics 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, J. Mol. Biol. 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, Proteins 33: 88-96) or combinatorial extension (Shindyalov and Bourne, 1998, Protein Engineering 11: 739-747), and implementation of these algorithms can additionally be utilized to query structure databases with a structure of interest in order to discover possible structural homologs (e.g., Holm and Park, 2000, Bioinformatics 16: 566-567).

In describing the variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Different alterations. Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants: "Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

Variants

The present invention provides variants with cutinase activity of a parent cutinase, comprising an alteration at one or more (e.g. several) positions corresponding to positions: 36, 37, 40, 78, 90, 114, 150, 196, 216, or 217 of SEQ ID NO: 2, wherein the alteration is a substitution for positions 40, 78, 90, 114, 150, 196 and 216, and a deletion for positions 36, 37 and 217, and wherein the variant has at least 75%, but less than 100% sequence identity to the mature polypeptide of SEQ ID NO: 2.

In one aspect, the variant has sequence identity of at least 75%, at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the parent cutinase.

In one aspect, the variant has at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the mature polypeptide of SEQ ID NO: 2 or amino acid 36 to 229 of SEQ ID No: 2.

In one aspect, the number of alterations in the variants of the present invention is 1-20, e.g., 1-10 and 1-5, such as 1, 2, 3, 4, 5, 6, 7, 8, 9, 10, 11, 12, 13, 14, 15, 16, 17, 18, 19 or 20 alterations.

In another aspect, a variant comprises an alteration at one or more (e.g., several) positions corresponding to positions 36, 37, 40, 78, 90, 114, 150, 196, 216 and 217. In another aspect, a variant comprises an alteration at two positions corresponding to any of positions 36, 37, 40, 78, 90, 114, 150, 196, 216 and 217. In another aspect, a variant comprises an alteration at three positions corresponding to any of positions 36, 37, 40, 78, 90, 114, 150, 196, 216 and 217. In another aspect, a variant comprises an alteration at four positions corresponding to any of positions 36, 37, 40, 78, 90, 114, 150, 196, 216 and 217. In another aspect, a variant comprises an alteration at five positions corresponding to any of positions 36, 37, 40, 78, 90, 114, 150, 196, 216 and 217. In another aspect, a variant comprises an alteration at six positions corresponding to any of positions 36, 37, 40, 78, 90, 114, 150, 196, 216 and 217. In another aspect, a variant comprises an alteration at seven positions corresponding to any of positions 36, 37, 40, 78, 90, 114, 150, 196, 216 and 217. In another aspect, a variant comprises an alteration at eight positions corresponding to any of positions 36, 37, 40, 78, 90, 114, 150, 196, 216 and 217. In another aspect, a variant comprises an alteration at nine positions corresponding to any of positions 36, 37, 40, 78, 90, 114, 150, 196, 216 and 217. In another aspect, a variant comprises an alteration at each position corresponding to positions 36, 37, 40, 78, 90, 114, 150, 196, 216 and 217.

In another aspect, the variant comprises or consists of a substitution at a position corresponding to position 216. In another aspect, the amino acid at a position corresponding to position 216 is substituted with Ala, Asn, Asp, Cys, Gln, Glu, Gly, His, Ile, Leu, Lys, Met, Phe, Pro, Ser, Thr, Trp, Tyr, or Val, preferably with Pro. In another aspect, the variant comprises or consists of the substitution R216P of the mature polypeptide of SEQ ID NO: 2.

In another aspect, the variant comprises or consists of a deletion at a position corresponding to position 217. In another aspect, the amino acid at a position corresponding to position 217 is deleted. In another aspect, the variant comprises or consists of the deletion G217* of the mature polypeptide of SEQ ID NO: 2.

In another aspect, the variant comprises or consists of a substitution at a position corresponding to position 150. In another aspect, the amino acid at a position corresponding to position 150 is substituted with Ala, Arg, Asn, Asp, Cys, Gln, Glu, Gly, His, Ile, Leu, Lys, Met, Phe, Pro, Ser, Thr, Trp, or Tyr, preferably with Ile. In another aspect, the variant comprises or consists of the substitution V150I of the mature polypeptide of SEQ ID NO: 2.

In another aspect, the variant comprises or consists of a substitution at a position corresponding to position 196. In another aspect, the amino acid at a position corresponding to position 196 is substituted with Arg, Asn, Asp, Cys, Gln, Glu, Gly, His, Ile, Leu, Lys, Met, Phe, Pro, Ser, Thr, Trp, Tyr, or Val, preferably with Leu. In another aspect, the variant comprises or consists of the substitution A196L of the mature polypeptide of SEQ ID NO: 2.

In another aspect, the variant comprises or consists of a deletion at a position corresponding to position 36. In another aspect, the amino acid at a position corresponding to position 36 is deleted. In another aspect, the variant comprises or consists of the deletion Q36* of the mature polypeptide of SEQ ID NO: 2.

In another aspect, the variant comprises or consists of a deletion at a position corresponding to position 37. In another aspect, the amino acid at a position corresponding to position 37 is deleted. In another aspect, the variant comprises or consists of the deletion L37* of the mature polypeptide of SEQ ID NO: 2.

In another aspect, the variant comprises or consists of a substitution at a position corresponding to position 78. In another aspect, the amino acid at a position corresponding to position 78 is substituted with Arg, Asn, Asp, Cys, Gln, Glu, Gly, His, Ile, Leu, Lys, Met, Phe, Pro, Ser, Thr, Trp, Tyr, or Val, preferably with Cys. In another aspect, the variant comprises or consists of the substitution A78C of the mature polypeptide of SEQ ID NO: 2.

In another aspect, the variant comprises or consists of a substitution at a position corresponding to position 90. In another aspect, the amino acid at a position corresponding to position 90 is substituted with Ala, Arg, Asn, Asp, Cys, Gln, Glu, Gly, His, Leu, Lys, Met, Phe, Pro, Ser, Thr, Trp, Tyr, or Val, preferably with Cys. In another aspect, the variant comprises or consists of the substitution I90C of the mature polypeptide of SEQ ID NO: 2.

In another aspect, the variant comprises or consists of a substitution at a position corresponding to position 114. In another aspect, the amino acid at a position corresponding to position 114 is substituted with Ala, Arg, Asp, Cys, Gln, Glu, Gly, His, Ile, Leu, Lys, Met, Phe, Pro, Ser, Thr, Trp, Tyr, or Val, preferably with Ala. In another aspect, the variant comprises or consists of the substitution N114A of the mature polypeptide of SEQ ID NO: 2.

In another aspect, the variant comprises or consists of a substitution at a position corresponding to position 40. In another aspect, the amino acid at a position corresponding to position 40 is substituted with Ala, Arg, Asn, Asp, Cys, Gln, Glu, Gly, His, Leu, Lys, Met, Phe, Pro, Ser, Thr, Trp, Tyr, or Val, preferably with Val. In another aspect, the variant comprises or consists of the substitution I40V of the mature polypeptide of SEQ ID NO: 2.

In another aspect, the variant comprises or consists of an alteration at positions corresponding to positions 36+37, 36+40, 36+78, 36+90, 36+114, 36+150, 36+196, 36+216, 36+217, 37+40, 37+78, 37+90, 37+114, 37+150, 37+196, 37+216, 37+217, 40+78, 40+90, 40+114, 40+150, 40+196, 40+216, 40+217, 78+90, 78+114, 78+150, 78+196, 78+216, 78+217, 90+114, 90+150, 90+196, 90+216, 90+217, 114+150, 114+196, 114+216, 114+217, 150+196, 150+216, 150+217, 196+216, 196+217, 216+217, such as those described above.

In another aspect, the variant comprises or consists of alterations at positions corresponding to positions 150+216+217, 196+216+217, 36+216+217, 37+216+217, 78+216+217, 90+216+217, 114+216+217, 40+216+217, 150+196+216, 36+150+216, 37+150+216, 78+150+216, 90+150+216, 114+150+216, 40+150+216, 36+196+216, 37+196+216, 78+196+216, 90+196+216, 114+196+216, 40+196+216, 36+37+216, 36+78+216, 36+90+216, 36+114+216, 36+40+216, 37+78+216, 37+90+216, 37+114+216, 37+40+216, 78+90+216, 78+114+216, 40+78+216, 90+114+216, 40+90+216, 40+114+216, 150+196+217, 36+150+217, 37+150+217, 78+150+217, 90+150+217, 114+150+217, 40+150+217, 36+196+217, 37+196+217, 78+196+217, 90+196+217, 114+196+217, 40+196+217, 36+37+217, 36+78+217, 36+90+217, 36+114+217, 36+40+217, 37+78+217, 37+90+217, 37+114+217, 37+40+217, 78+90+217, 78+114+217, 40+78+217, 90+114+217, 40+90+217, 40+114+217, 36+150+196, 37+150+196, 78+150+196, 90+150+196, 114+150+196, 40+150+196, 36+37+196, 36+78+196, 36+90+196, 36+114+196, 36+40+196, 37+78+196, 37+90+196, 37+114+196, 37+40+196, 78+90+196, 78+114+196, 40+78+196, 90+114+196, 40+90+196, 40+114+196, 36+37+78, 36+37+90, 36+37+114, 36+37+40, 36+78+90, 36+78+114, 36+40+78, 36+90+114, 36+40+90, 36+40+114, 37+78+90, 37+78+114, 37+40+78, 37+90+114, 37+40+90, 37+40+114, 78+90+114, 40+78+90, 40+78+114, 40+90+114, such as those described above.

In another aspect, the variant comprises or consists of alterations at positions corresponding to positions 150+196+216+217, 36+150+216+217, 37+150+216+217, 78+150+216+217, 90+150+216+217, 114+150+216+217, 40+150+216+217, 36+196+216+217, 37+196+216+217, 78+196+216+217, 90+196+216+217, 114+196+216+217, 40+196+216+217, 36+37+216+217, 36+78+216+217, 36+90+216+217, 36+114+216+217, 36+40+216+217, 37+78+216+217, 37+90+216+217, 37+114+216+217, 37+40+216+217, 78+90+216+217, 78+114+216+217, 40+78+216+217, 90+114+216+217, 40+90+216+217, 40+114+216+217, 36+150+196+216, 37+150+196+216, 150+78+196+216, 150+90+196+216, 150+114+196+216, 150+40+196+216, 36+37+150+216, 36+78+150+216, 36+90+150+216, 36+114+150+216, 36+40+150+216, 37+78+150+216, 37+90+150+216, 37+114+150+216, 37+40+150+216, 78+90+150+216, 78+114+150+216, 40+78+150+216, 90+114+150+216, 40+90+150+216, 40+114+150+216, 36+37+196+216, 36+78+196+216, 36+90+196+216, 36+114+196+216, 36+40+196+216, 37+78+196+216, 37+90+196+216, 37+114+196+216, 37+40+196+216, 78+90+196+216, 78+114+196+216, 40+78+196+216, 90+114+196+216, 40+90+196+216, 40+114+196+216, 36+37+78+216, 36+37+90+216, 36+37+114+216, 36+37+40+216, 36+78+90+216, 36+78+114+216, 36+40+78+216, 36+90+114+216, 36+40+90+216, 36+40+114+216, 37+78+90+216, 37+78+114+216, 37+40+78+216, 37+90+114+216, 37+40+90+216, 37+40+114+216, 78+90+114+216, 40+78+90+216, 40+78+114+216, 40+90+114+216, 36+150+196+217, 37+150+196+217, 78+150+196+217, 90+150+196+217, 114+150+196+217, 40+150+196+217, 36+37+150+217, 36+78+150+217, 36+90+150+217, 36+114+150+217, 36+40+150+217, 37+78+150+217, 37+90+150+217, 37+114+150+217, 37+40+150+217, 78+90+150+217, 78+114+150+217, 40+78+150+217, 90+114+150+217, 40+90+150+217, 40+114+150+217, 36+37+196+217, 36+78+196+217, 36+90+196+217, 36+114+196+217, 36+40+196+217, 37+78+196+217, 37+90+196+217, 37+114+196+217, 37+40+196+217, 78+90+196+217, 78+114+196+217, 40+78+196+217, 90+114+196+217, 40+90+196+217, 40+114+196+217, 36+37+78+217, 36+37+90+217, 36+37+114+217, 36+37+40+217, 36+78+90+217, 36+78+114+217, 36+40+78+217, 36+90+114+217, 36+40+90+217, 36+40+114+217, 37+78+90+217, 37+78+114+217, 37+40+78+217, 37+90+114+217, 37+40+90+217, 37+40+114+217, 78+90+114+217, 40+78+90+217, 40+78+114+217, 40+90+114+217, 36+37+150+196, 36+78+150+196, 36+90+150+196, 36+114+150+196, 36+40+150+196, 37+78+150+196, 37+90+150+196, 37+114+150+196, 37+40+150+196, 78+90+150+196, 78+114+150+196, 40+78+150+196, 90+114+150+196, 40+90+150+196, 40+114+150+196, 36+37+78+150, 36+37+90+150, 36+37+114+150, 36+37+40+150, 36+78+90+150, 36+78+114+150, 36+40+78+150, 36+90+114+150, 36+40+90+150, 36+40+114+150, 37+78+90+150, 37+78+114+150, 37+40+78+150, 37+90+114+150, 37+40+90+150, 37+40+114+150, 78+90+114+150, 40+78+90+150, 40+78+114+150, 40+90+114+150, 36+37+78+196, 36+37+90+196, 36+37+114+196, 36+37+40+196, 36+78+90+196, 36+78+114+196, 36+40+78+196, 36+90+114+196, 36+40+90+196, 36+40+114+196, 37+78+90+196, 37+78+114+196, 37+40+78+196, 37+90+114+196, 37+40+90+196, 37+40+114+196, 78+90+114+196, 40+78+90+196, 40+78+114+196, 40+90+114+196, 36+37+78+90, 36+37+78+114, 36+37+40+78, 36+37+90+114, 36+37+40+90, 36+37+40+114, 36+78+90+114, 36+40+78+90, 36+40+78+114, 36+40+90+114, 37+78+90+114, 37+40+78+90, 37+40+78+114, 37+40+90+114, 40+78+90+114, such as those described above.

In another aspect, the variant comprises or consists of alterations at positions corresponding to positions 36+150+196+216+217, 37+150+196+216+217, 78+150+196+216+217, 90+150+196+216+217, 114+150+196+216+217, 40+150+196+216+217, 36+37+150+216+217, 36+78+150+216+217, 36+90+150+216+217, 36+114+150+216+217, 36+40+150+216+217, 37+78+150+216+217, 37+90+150+216+217, 37+114+150+216+217, 37+40+150+216+217, 78+90+150+216+217, 78+114+150+216+217, 40+78+150+216+217, 90+114+150+216+217, 40+90+150+216+217, 40+114+150+216+217, 36+37+196+216+217, 36+78+196+216+217, 36+90+196+216+217, 36+114+196+216+217, 36+40+196+216+217, 37+78+196+216+217, 37+90+196+216+217, 37+114+196+216+217, 37+40+196+216+217, 78+90+196+216+217, 78+114+196+216+217, 40+78+196+216+217, 90+114+196+216+217, 40+90+196+216+217, 40+114+196+216+217, 36+37+78+216+217, 36+37+90+216+217, 36+37+114+216+217, 36+37+40+216+217, 36+78+90+216+217, 36+78+114+216+217, 36+40+78+216+217, 36+90+114+216+217, 36+40+90+216+217, 36+40+114+216+217, 37+78+90+216+217, 37+78+114+216+217, 37+40+78+216+217, 37+90+114+216+217, 37+40+90+216+217, 37+40+114+216+217, 78+90+114+216+217, 40+78+90+216+217, 40+78+114+216+217, 40+90+114+216+217, 36+37+150+196+216, 36+78+150+196+216, 36+90+150+196+216, 36+114+150+196+216, 36+40+150+196+216, 37+78+150+196+216, 37+90+150+196+216, 37+114+150+196+216, 37+40+150+196+216, 78+90+150+196+216, 78+114+150+196+216, 40+78+150+

196+216, 90+114+150+196+216, 40+90+150+196+216, 40+114+150+196+216, 36+37+78+150+216, 36+37+90+150+216, 36+37+114+150+216, 36+37+40+150+216, 36+78+90+150+216, 36+78+114+150+216, 36+40+78+150+216, 36+90+114+150+216, 36+40+90+150+216, 36+40+114+150+216, 37+78+90+150+216, 37+78+114+150+216, 37+40+78+150+216, 37+90+114+150+216, 37+40+90+150+216, 37+40+114+150+216, 78+90+114+150+216, 40+78+90+150+216, 40+78+114+150+216, 40+90+114+150+216, 36+37+78+196+216, 36+37+90+196+216, 36+37+114+196+216, 36+37+40+196+216, 36+78+90+196+216, 36+78+114+196+216, 36+40+78+196+216, 36+90+114+196+216, 36+40+90+196+216, 36+40+114+196+216, 37+78+90+196+216, 37+78+114+196+216, 37+40+78+196+216, 37+90+114+196+216, 37+40+90+196+216, 37+40+114+196+216, 78+90+114+196+216, 40+78+90+196+216, 40+78+114+196+216, 40+90+114+196+216, 36+37+78+90+216, 36+37+78+114+216, 36+37+40+78+216, 36+37+90+114+216, 36+37+40+90+216, 36+37+40+114+216, 36+78+90+114+216, 36+40+78+90+216, 36+40+78+114+216, 36+40+90+114+216, 37+78+90+114+216, 37+40+78+90+216, 37+40+78+114+216, 37+40+90+114+216, 40+78+90+114+216, 36+37+150+196+217, 36+78+150+196+217, 36+90+150+196+217, 36+114+150+196+217, 36+40+150+196+217, 37+78+150+196+217, 37+90+150+196+217, 37+114+150+196+217, 37+40+150+196+217, 78+90+150+196+217, 78+114+150+196+217, 40+78+150+196+217, 90+114+150+196+217, 40+90+150+196+217, 40+114+150+196+217, 36+37+78+150+217, 36+37+90+150+217, 36+37+114+150+217, 36+37+40+150+217, 36+78+90+150+217, 36+78+114+150+217, 36+40+78+150+217, 36+90+114+150+217, 36+40+90+150+217, 36+40+114+150+217, 37+78+90+150+217, 37+78+114+150+217, 37+40+78+150+217, 37+90+114+150+217, 37+40+90+150+217, 37+40+114+150+217, 78+90+114+150+217, 40+78+90+150+217, 40+78+114+150+217, 40+90+114+150+217, 36+37+78+196+217, 36+37+90+196+217, 36+37+114+196+217, 36+37+40+196+217, 36+78+90+196+217, 36+78+114+196+217, 36+40+78+196+217, 36+90+114+196+217, 36+90+150+196+217, 36+40+114+196+217, 37+78+90+196+217, 37+78+114+196+217, 37+40+78+196+217, 37+90+114+196+217, 37+40+90+196+217, 37+40+114+196+217, 78+90+114+196+217, 40+78+90+196+217, 40+78+114+196+217, 40+90+114+196+217, 36+37+78+90+217, 36+37+78+114+217, 36+37+40+78+217, 36+37+90+114+217, 36+37+40+90+217, 36+37+40+114+217, 36+78+90+114+217, 36+40+78+90+217, 36+40+78+114+217, 36+40+90+114+217, 37+78+90+114+217, 37+40+78+90+217, 37+40+78+114+217, 37+40+90+114+217, 40+78+90+114+217, 36+37+78+150+196, 36+37+90+150+196, 36+37+114+150+196, 36+37+40+150+196, 36+78+90+150+196, 36+78+114+150+196, 36+40+78+150+196, 36+90+114+150+196, 36+40+90+150+196, 36+40+114+150+196, 37+78+90+150+196, 37+78+114+150+196, 37+40+78+150+196, 37+90+114+150+196, 37+40+90+150+196, 37+40+114+150+196, 78+90+114+150+196, 40+78+90+150+196, 40+78+114+150+196, 40+90+114+150+196, 36+37+78+90+150, 36+37+78+114+150, 36+37+40+78+150, 36+37+90+114+150, 36+37+40+90+150, 36+37+40+114+150, 36+78+90+114+150, 36+40+78+90+150, 36+40+78+114+150, 36+40+90+114+150, 37+78+90+114+150, 37+40+78+90+150, 37+40+78+114+150, 37+40+90+114+150, 40+78+90+114+150, 36+37+78+90+196, 36+37+78+114+196, 36+37+40+78+196, 36+37+90+114+196, 36+37+40+90+196, 36+37+40+114+196, 36+78+90+114+196, 36+40+78+90+196, 36+40+78+114+196, 36+40+90+114+196, 36+40+78+90+114+196, 36+40+78+90+114+196, 36+40+78+90+114+196, 36+40+78+90+114+196, 36+40+78+90+114+196, 36+40+

90+114+196, 37+78+90+114+196, 37+40+78+90+196, 37+40+78+114+196, 37+40+90+114+196, 40+78+90+114+196, 36+37+78+90+114, 36+37+40+78+90, 36+37+40+78+114, 36+37+40+90+114, 36+40+78+90+114, 37+40+78+90+114, such as those described above.

In another aspect, the variant comprises or consists of alterations at positions corresponding to positions 36+37+150+196+216+217, 36+78+150+196+216+217, 36+90+150+196+216+217, 36+114+150+196+216+217, 36+40+150+196+216+217, 37+78+150+196+216+217, 37+90+150+196+216+217, 37+114+150+196+216+217, 37+40+150+196+216+217, 78+90+150+196+216+217, 78+114+150+196+216+217, 40+78+150+196+216+217, 90+114+150+196+216+217, 40+90+150+196+216+217, 40+114+150+196+216+217, 36+37+78+150+216+217, 36+37+90+150+216+217, 36+37+114+150+216+217, 36+37+40+150+216+217, 36+78+90+150+216+217, 36+78+114+150+216+217, 36+40+78+150+216+217, 36+90+114+150+216+217, 36+40+90+150+216+217, 36+40+114+150+216+217, 37+78+90+150+216+217, 37+78+114+150+216+217, 37+40+78+150+216+217, 37+90+114+150+216+217, 37+40+90+150+216+217, 37+40+114+150+216+217, 78+90+114+150+216+217, 40+78+90+150+216+217, 40+78+114+150+216+217, 40+90+114+150+216+217, 36+37+78+196+216+217, 36+37+90+196+216+217, 36+37+114+196+216+217, 36+37+40+196+216+217, 216+36+78+90+196+216+217, 36+78+114+196+216+217, 36+40+78+196+216+217, 36+90+114+196+216+217, 36+40+90+196+216+217, 36+40+114+196+216+217, 37+78+90+196+216+217, 37+78+114+196+216+217, 37+40+78+196+216+217, 37+90+114+196+216+217, 37+40+90+196+216+217, 37+40+114+196+216+217, 78+90+114+196+216+217, 40+78+90+196+216+217, 40+78+114+196+216+217, 40+90+114+196+216+217, 36+37+78+90+216+217, 36+37+78+114+216+217, 36+37+40+78+216+217, 36+37+90+114+216+217, 36+37+40+90+216+217, 36+37+40+114+216+217, 36+78+90+114+216+217, 36+40+78+90+216+217, 36+40+78+114+216+217, 36+40+90+114+216+217, 37+78+90+114+216+217, 37+40+78+90+216+217, 37+40+78+114+216+217, 37+40+90+114+216+217, 40+78+90+114+216+217, 36+37+78+150+196+216, 36+37+90+150+196+216, 36+37+114+150+196+216, 36+37+40+150+196+216, 36+78+90+150+196+216, 36+78+114+150+196+216, 36+40+78+150+196+216, 36+90+114+150+196+216, 36+40+90+150+196+216, 36+40+114+150+196+216, 37+78+90+150+196+216, 37+78+114+150+196+216, 37+40+78+150+196+216, 37+90+114+150+196+216, 37+40+90+150+196+216, 37+40+114+150+196+216, 78+90+114+150+196+216, 40+78+90+150+196+216, 40+78+114+150+196+216, 40+90+114+150+196+216, 36+37+78+90+150+216, 36+37+78+114+150+216, 36+37+40+78+150+216, 36+37+90+114+150+216, 36+37+40+90+150+216, 36+37+40+114+150+216, 36+78+90+114+150+216, 36+40+78+90+150+216, 36+40+78+114+150+216, 36+40+90+114+150+216, 37+78+90+114+150+216, 37+40+78+90+150+216, 37+40+78+114+150+216, 37+40+90+114+150+216, 40+78+90+114+150+216, 36+37+78+90+196+216, 36+37+78+114+196+216, 36+37+40+78+196+216, 36+37+90+114+196+216, 36+37+40+90+196+216, 36+37+40+114+196+216, 36+78+90+114+196+216, 36+40+78+90+196+216, 36+40+78+114+196+216, 36+40+90+114+196+216, 37+78+90+114+196+216, 37+40+78+90+196+216, 37+40+78+114+196+216, 37+40+90+114+196+216, 40+78+90+114+196+216, 36+37+78+90+114+216, 36+37+40+78+90+216, 36+37+40+78+114+216, 36+37+40+90+114+216, 36+40+78+90+114+216, 37+40+78+90+114+216, 36+37+

78+150+196+217, 36+37+90+150+196+217, 36+37+114+ 150+196+217, 36+37+40+150+196+217, 36+78+90+150+ 196+217, 36+78+114+150+196+217, 36+40+78+150+196+ 217, 36+90+114+150+196+217, 36+40+90+150+196+217, 36+40+114+150+196+217, 37+78+90+150+196+217, 37+78+114+150+196+217, 37+40+78+150+196+217, 37+90+114+150+196+217, 37+40+90+150+196+217, 37+40+114+150+196+217, 78+90+114+150+196+217, 40+78+90+150+196+217, 40+78+114+150+196+217, 40+90+114+150+196+217, 36+37+78+90+150+217, 36+37+78+114+150+217, 36+37+40+78+150+217, 36+37+ 90+114+150+217, 36+37+40+90+150+217, 36+37+40+ 114+150+217, 36+78+90+114+150+217, 36+40+78+90+ 150+217, 36+40+78+114+150+217, 36+40+90+114+150+ 217, 37+78+90+114+150+217, 37+40+78+90+150+217, 37+40+78+114+150+217, 37+40+90+114+150+217, 40+78+90+114+150+217, 36+37+78+90+196+217, 36+37+ 78+114+196+217, 36+37+40+78+196+217, 36+37+90+ 114+196+217, 36+37+40+90+196+217, 36+37+40+114+ 196+217, 36+78+90+114+196+217, 36+40+78+90+196+ 217, 36+40+78+114+196+217, 36+40+90+114+196+217, 37+78+90+114+196+217, 37+40+78+90+196+217, 37+40+ 78+114+196+217, 37+40+90+114+196+217, 40+78+90+ 114+196+217, 36+37+78+90+114+217, 36+37+40+78+90+ 217, 36+37+40+78+114+217, 36+37+40+90+114+217, 36+40+78+90+114+217, 37+40+78+90+114+217, 36+37+ 78+90+150+196, 36+37+78+114+150+196, 36+37+40+78+ 150+196, 36+37+90+114+150+196, 36+37+40+90+150+ 196, 36+37+40+114+150+196, 36+78+90+114+150+196, 36+40+78+90+150+196, 36+40+78+114+150+196, 36+40+ 90+114+150+196, 37+78+90+114+150+196, 37+40+78+ 90+150+196, 37+40+78+114+150+196, 37+40+90+114+ 150+196, 40+78+90+114+150+196, 36+37+78+90+114+ 150+1500, 36+37+40+78+90+150, 36+37+40+78+114+ 150, 36+37+40+90+114+150, 36+40+78+90+114+150, 37+40+78+90+114+150, 36+37+78+90+114+196, 36+37+ 40+78+90+196, 36+37+40+78+114+196, 36+37+40+90+ 114+196, 36+40+78+90+114+196, 37+40+78+90+114+ 196, 36+37+40+78+90+114, such as those described above.

In another aspect, the variant comprises or consists of alterations at positions corresponding to positions 36+37+ 78+150+196+216+217, 36+37+90+150+196+216+217, 36+37+114+150+196+216+217, 36+37+40+150+196+216+ 217, 36+78+90+150+196+216+217, 36+78+114+150+196+ 216+217, 36+40+78+150+196+216+217, 36+90+114+150+ 196+216+217, 36+40+90+150+196+216+217, 40+114+ 150+196+216+217, 37+78+90+150+196+216+217, 37+78+ 114+150+196+216+217, 37+40+78+150+196+216+217, 37+90+114+150+196+216+217, 37+40+90+150+196+216+ 217, 37+40+114+150+196+216+217, 78+90+114+150+ 196+216+217, 40+78+90+150+196+216+217, 40+78+114+ 150+196+216+217, 40+90+114+150+196+216+217, 36+37+78+90+150+216+217, 36+37+78+114+150+216+ 217, 36+37+40+78+150+216+217, 36+37+90+114+150+ 216+217, 36+37+40+90+150+216+217, 36+37+40+114+ 150+216+217, 36+78+90+114+150+216+217, 36+40+78+ 90+150+216+217, 36+40+78+114+150+216+217, 36+40+ 90+114+150+216+217, 37+78+90+114+150+216+217, 37+40+78+90+150+216+217, 37+40+78+114+150+216+ 217, 37+40+90+114+150+216+217, 40+78+90+114+150+ 216+217, 36+37+78+90+196+216+217, 36+37+78+114+ 196+216+217, 36+37+40+78+196+216+217, 36+37+90+ 114+196+216+217, 36+37+40+90+196+216+217, 36+37+ 40+114+196+216+217, 36+78+90+114+196+216+217, 36+40+78+90+196+216+217, 36+40+78+114+196+216+ 217, 36+40+90+114+196+216+217, 37+78+90+114+196+ 216+217, 37+40+78+90+196+216+217, 37+40+78+114+ 196+216+217, 37+40+90+114+196+216+217, 40+78+90+ 114+196+216+217, 36+37+78+90+114+216+217, 36+37+ 40+78+90+216+217, 36+37+40+78+114+216+217, 36+37+ 40+90+114+216+217, 36+40+78+90+114+216+217, 37+40+78+90+114+216+217, 36+37+78+90+150+196+ 216, 36+37+78+114+150+196+216, 36+37+40+78+150+ 196+216, 36+37+90+114+150+196+216, 36+37+40+90+ 150+196+216, 36+37+40+114+150+196+216, 36+78+90+ 114+150+196+216, 36+40+78+90+150+196+216, 36+40+ 78+114+150+196+216, 36+40+90+114+150+196+216, 37+78+90+114+150+196+216, 37+40+78+90+150+196+ 216, 37+40+78+114+150+196+216, 37+40+90+114+150+ 196+216, 40+78+90+114+150+196+216, 36+37+78+90+ 114+150+216, 36+37+40+78+90+150+216, 36+37+40+78+ 114+150+216, 36+37+40+90+114+150+216, 36+40+78+ 90+114+150+216, 37+40+78+90+114+150+216, 36+37+ 78+90+114+196+216, 36+37+40+78+90+196+216, 36+37+ 40+78+114+196+216, 36+37+40+90+114+196+216, 36+40+78+90+114+196+216, 37+40+78+90+114+196+ 216, 36+37+40+78+90+114+216, 36+37+78+90+150+196+ 217, 36+37+78+114+150+196+217, 36+37+40+78+150+ 196+217, 36+37+90+114+150+196+217, 36+37+40+90+ 150+196+217, 36+37+40+114+150+196+217, 36+78+90+ 114+150+196+217, 36+40+78+90+150+196+217, 36+40+ 78+114+150+196+217, 36+40+90+114+150+196+217, 37+78+90+114+150+196+217, 37+40+78+90+150+196+ 217, 37+40+78+114+150+196+217, 37+40+90+114+150+ 196+217, 40+78+90+114+150+196+217, 36+37+78+90+ 114+150+217, 36+37+40+78+90+150+217, 36+37+40+78+ 114+150+217, 36+37+40+90+114+150+217, 36+40+78+ 90+114+150+217, 37+40+78+90+114+150+217, 36+37+ 78+90+114+196+217, 36+37+40+78+90+196+217, 36+37+ 40+78+114+196+217, 36+37+40+90+114+196+217, 36+40+78+90+114+196+217, 37+40+78+90+114+196+ 217, 36+37+40+78+90+114+217, 36+37+78+90+114+150+ 196, 36+37+40+78+90+150+196, 36+37+40+78+114+150+ 196, 36+37+40+90+114+150+196, 36+40+78+90+114+ 150+196, 37+40+78+90+114+150+196, 36+37+40+78+90+ 114+150, 36+37+40+78+90+114+196, such as those described above.

In another aspect, the variant comprises or consists of alterations at positions corresponding to positions 36+37+ 78+90+150+196+216+217, 36+37+78+114+150+196+216+ 217, 36+37+40+78+150+196+216+217, 36+37+90+114+ 150+196+216+217, 36+37+40+90+150+196+216+217, 36+37+40+114+150+196+216+217, 36+78+90+114+150+ 196+216+217, 36+40+78+90+150+196+216+217, 36+40+ 78+114+150+196+216+217, 36+40+90+114+150+196+ 216+217, 37+78+90+114+150+196+216+217, 37+40+78+ 90+150+196+216+217, 37+40+78+114+150+196+216+ 217, 37+40+90+114+150+196+216+217, 40+78+90+114+ 150+196+216+217, 36+37+78+90+114+150+216+217, 36+37+40+78+90+150+216+217, 36+37+40+78+114+ 150+216+217, 36+37+40+90+114+150+216+217, 36+40+ 78+90+114+150+216+217, 37+40+78+90+114+150+216+ 217, 36+37+78+90+114+196+216+217, 36+37+40+78+90+ 196+216+217, 36+37+40+78+114+196+216+217, 36+37+ 40+90+114+196+216+217, 36+40+78+90+114+196+216+ 217, 37+40+78+90+114+196+216+217, 36+37+40+78+90+ 114+216+217, 36+37+78+90+114+150+196+216, 36+37+ 40+78+90+150+196+216, 36+37+40+78+114+150+196+ 216, 36+37+40+90+114+150+196+216, 36+40+78+90+ 114+150+196+216, 37+40+78+90+114+150+196+216, 36+37+40+78+90+114+150+216, 36+37+40+78+90+114+ 196+216, 36+37+78+90+114+150+196+217, 36+37+40+ 78+90+150+196+217, 36+37+40+78+114+150+196+217, 36+37+40+90+114+150+196+217, 36+40+78+90+114+

150+196+217, 37+40+78+90+114+150+196+217, 36+37+ 40+78+90+114+150+217, 36+37+40+78+90+114+196+ 217, 36+37+40+78+90+114+150+196, such as those described above.

In another aspect, the variant comprises or consists of alterations at positions corresponding to positions 36+37+ 78+90+114+150+196+216+217, 36+37+40+78+90+150+ 196+216+217, 36+37+40+78+114+150+196+216+217, 36+37+40+90+114+150+196+216+217, 36+40+78+90+ 114+150+196+216+217, 37+40+78+90+114+150+196+ 216+217, 36+37+40+78+90+114+150+216+217, 36+37+ 40+78+90+114+196+216+217, 36+37+40+78+90+114+ 150+196+216, 36+37+40+78+90+114+150+196+217, such as those described above.

In another aspect, the variant comprises or consists of alterations at positions corresponding to positions 36+37+ 40+78+90+114+150+196+216+217, such as those described above.

In another aspect, the variant comprises or consists of one or more (e.g., several) substitutions selected from the group consisting of Q36*, L37*, I40V, A78C, I90C, N114A, V150I, A196L, R216P and G217*.

In another aspect, the variant comprises or consists of the substitutions Q36*+L37*, Q36*+I40V, Q36*+A78C, Q36*+I90C, Q36*+N114A, Q36*+V150I, Q36*+A196L, Q36*+R216P, Q36*+G217*, L37*+I40V, L37*+A78C, L37*+I90C, L37*+N114A, L37*+V150I, L37*+A196L, L37*+R216P, L37*+G217*, I40V+A78C, I40V+I90C, I40V+N114A, I40V+V150I, I40V+A196L, I40V+R216P, I40V+G217*, A78C+I90C, A78C+N114A, A78C+V150I, A78C+A196L, A78C+R216P, A78C+G217*, I90C+N114A, I90C+V150I, I90C+A196L, I90C+R216P, I90C+G217*, N114A+V150I, N114A+A196L, N114A+R216P, N114A+ G217*, V150I+A196L, V150I+R216P, V150I+G217*, A196L+R216P, A196L+G217*, R216P+G217* of the mature polypeptide of SEQ ID NO: 2.

In another aspect, the variant comprises or consists of the substitutions V150I+R216P+G217*, A196L+R216P+ G217*, Q36*+R216P+G217*, L37*+R216P+G217*, A78C+R216P+G217*, I90C+R216P+G217*, N114A+ R216P+G217*, I40V+R216P+G217*, V150I+A196L+ R216P, Q36*+V150I+R216P, L37*+V150I+R216P, A78C+ V150I+R216P, I90C+V150I+R216P, N114A+V150I+ R216P, I40V+V150I+R216P, Q36*+A196L+R216P, L37*+ A196L+R216P, A78C+A196L+R216P, I90C+A196L+ R216P, N114A+A196L+R216P, I40V+A196L+R216P, Q36*+L37*+R216P, Q36*+A78C+R216P, Q36*+I90C+ R216P, Q36*+N114A+R216P, Q36*+I40V+R216P, L37*+ A78C+R216P, L37*+I90C+R216P, L37*+N114A+R216P, L37*+I40V+R216P, A78C+I90C+R216P, A78C+N114A+ R216P, I40V+A78C+R216P, I90C+N114A+R216P, I40V+ I90C+R216P, I40V+N114A+R216P, V150I+A196L+ G217*, Q36*+V150I+G217*, L37*+V150I+G217*, A78C+V150I+G217*, I90C+V150I+G217*, N114A+ V150I+G217*, I40V+V150I+G217*, Q36*+A196L+ G217*, L37*+A196L+G217*, A78C+A196L+G217*, I90C+A196L+G217*, N114A+A196L+G217*, I40V+ A196L+G217*, Q36*+L37*+G217*, Q36*+A78C+G217*, Q36*+I90C+G217*, Q36*+N114A+G217*, Q36*+I40V+ G217*, L37*+A78C+G217*, L37*+I90C+G217*, L37*+ N114A+G217*, L37*+I40V+G217*, A78C+I90C+G217*, A78C+N114A+G217*, I40V+A78C+G217*, I90C+ N114A+G217*, I40V+I90C+G217*, I40V+N114A+G217*, Q36*+V150I+A196L, L37*+V150I+A196L, A78C+ V150I+A196L, I90C+V150I+A196L, N114A+V150I+ A196L, I40V+V150I+A196L, Q36*+L37*+V150I, Q36*+ A78C+V150I, Q36*+I90C+V150I, Q36*+N114A+V150I, Q36*+I40V+V150I, L37*+A78C+V150I, L37*+I90C+ V150I, L37*+N114A+V150I, L37*+I40V+V150I, A78C+ I90C+V150I, A78C+N114A+V150I, I40V+A78C+V150I, I90C+N114A+V150I, I140V+I90C+V150I, I40V+N114A+ V150I, Q36*+L37*+A196L, Q36*+A78C+A196L, Q36*+ I90C+A196L, Q36*+N114A+A196L, Q36*+I40V+A196L, L37*+A78C+A196L, L37*+I90C+A196L, L37*+N114A+ A196L, L37*+I40V+A196L, A78C+I90C+A196L, A78C+ N114A+A196L, I40V+A78C+A196L, I90C+N114A+ A196L, I40V+I90C+A196L, I40V+N114A+A196L, Q36*+ L37*+A78C, Q36*+L37*+I90C, Q36*+L37*+N114A, Q36*+L37*+I40V, Q36*+A78C+I90C, Q36*+A78C+ N114A, Q36*+I40V+A78C, Q36*+I90C+N114A, Q36*+ I40V+I90C, Q36*+I40V+N114A, L37*+A78C+I90C, L37*+A78C+N114A, L37*+I40V+A78C, L37*+I90C+ N114A, L37*+I40V+I90C, L37*+I40V+N114A, A78C+ I90C+N114A, I40V+A78C+I90C, I40V+A78C+N114A, I40V+I90C+N114A of the mature polypeptide of SEQ ID NO: 2.

In another aspect, the variant comprises or consists of the substitutions V150I+A196L+R216P+G217*, Q36*+ V150I+R216P+G217*, L37*+V150I+R216P+G217*, A78C+V150I+R216P+G217*, I90C+V150I+R216P+ G217*, N114A+V150I+R216P+G217*, I40V+V150I+ R216P+G217*, Q36*+A196L+R216P+G217*, L37*+ A196L+R216P+G217*, A78C+A196L+R216P+G217*, I90C+A196L+R216P+G217*, N114A+A196L+R216P+ G217*, I40V+A196L+R216P+G217*, Q36*+L37*+ R216P+G217*, Q36*+A78C+R216P+G217*, Q36*+I90C+ R216P+G217*, Q36*+N114A+R216P+G217*, Q36*+ I40V+R216P+G217*, L37*+A78C+R216P+G217*, L37*+ I90C+R216P+G217*, L37*+N114A+R216P+G217*, L37*+I40V+R216P+G217*, A78C+I90C+R216P+G217*, A78C+N114A+R216P+G217*, I40V+A78C+R216P+ G217*, I90C+N114A+R216P+G217*, I40V+I90C+ R216P+G217*, I40V+N114A+R216P+G217*, Q36*+ V150I+A196L+R216P, L37*+V150I+A196L+R216P, V150I+A78C+A196L+R216P, V150I+I90C+A196L+ R216P, V150I+N114A+A196L+R216P, V150I+I40V+ A196L+R216P, Q36*+L37*+V150I+R216P, Q36*+A78C+ V150I+R216P, Q36*+I90C+V150I+R216P, Q36*+N114A+ V150I+R216P, Q36*+I40V+V150I+R216P, L37*+A78C+ V150I+R216P, L37*+I90C+V150I+R216P, L37*+N114A+ V150I+R216P, L37*+I40V+V150I+R216P, A78C+I90C+ V150I+R216P, A78C+N114A+V150I+R216P, I40V+ A78C+V150I+R216P, I90C+N114A+V150I+R216P, I40V+ I90C+V150I+R216P, I40V+N114A+V150I+R216P, Q36*+ L37*+A196L+R216P, Q36*+A78C+A196L+R216P, Q36*+I90C+A196L+R216P, Q36*+N114A+A196L+ R216P, Q36*+I40V+A196L+R216P, L37*+A78C+A196L+ R216P, L37*+I90C+A196L+R216P, L37*+N114A+ A196L+R216P, L37*+I40V+A196L+R216P, A78C+I90C+ A196L+R216P, A78C+N114A+A196L+R216P, I40V+ A78C+A196L+R216P, I90C+N114A+A196L+R216P, I40V+I90C+A196L+R216P, I40V+N114A+A196L+R216P, Q36*+L37*+A78C+R216P, Q36*+L37*+I90C+R216P, Q36*+L37*+N114A+R216P, Q36*+L37*+I40V+R216P, Q36*+A78C+I90C+R216P, Q36*+A78C+N114A+R216P, Q36*+I40V+A78C+R216P, Q36*+I90C+N114A+R216P, Q36*+I40V+I90C+R216P, Q36*+I40V+N114A+R216P, L37*+A78C+I90C+R216P, L37*+A78C+N114A+R216P, L37*+I40V+A78C+R216P, L37*+I90C+N114A+R216P, L37*+I40V+I90C+R216P, L37*+I40V+N114A+R216P, A78C+I90C+N114A+R216P, I40V+A78C+I90C+R216P, I40V+A78C+N114A+R216P, I40V+I90C+N114A+R216P, Q36*+V150I+A196L+G217*, L37*+V150I+A196L+ G217*, A78C+V150I+A196L+G217*, I90C+V150I+

A196L+G217*, N114A+V150I+A196L+G217*, I40V+V150I+A196L+G217*, Q36*+L37*+V150I+G217*, Q36*+A78C+V150I+G217*, Q36*+I90C+V150I+G217*, Q36*+N114A+V150I+G217*, Q36*+I40V+V150I+G217*, L37*+A78C+V150I+G217*, L37*+I90C+V150I+G217*, L37*+N114A+V150I+G217*, L37*+I40V+V150I+G217*, A78C+I90C+V150I+G217*, A78C+N114A+V150I+G217*, I40V+A78C+V150I+G217*, I90C+N114A+V150I+G217*, I40V+I90C+V150I+G217*, I40V+N114A+V150I+G217*, Q36*+L37*+A196L+G217*, Q36*+A78C+A196L+G217*, Q36*+I90C+A196L+G217*, Q36*+N114A+A196L+G217*, Q36*+I40V+A196L+G217*, L37*+A78C+A196L+G217*, L37*+I90C+A196L+G217*, L37*+N114A+A196L+G217*, L37*+I40V+A196L+G217*, A78C+I90C+A196L+G217*, A78C+N114A+A196L+G217*, I40V+A78C+A196L+G217*, I90C+N114A+A196L+G217*, I40V+I90C+A196L+G217*, I40V+N114A+A196L+G217*, Q36*+L37*+A78C+G217*, Q36*+L37*+I90C+G217*, Q36*+L37*+N114A+G217*, Q36*+L37*+I40V+G217*, Q36*+A78C+I90C+G217*, Q36*+A78C+N114A+G217*, Q36*+I40V+A78C+G217*, Q36*+I90C+N114A+G217*, Q36*+I40V+I90C+G217*, Q36*+I40V+N114A+G217*, L37*+A78C+I90C+G217*, L37*+A78C+N114A+G217*, L37*+I40V+A78C+G217*, L37*+I90C+N114A+G217*, L37*+I40V+I90C+G217*, L37*+I40V+N114A+G217*, A78C+I90C+N114A+G217*, I40V+A78C+I90C+G217*, I40V+A78C+N114A+G217*, I40V+I90C+N114A+G217*, Q36*+L37*+V150I+A196L, Q36*+A78C+V150I+A196L, Q36*+I90C+V150I+A196L, Q36*+N114A+V150I+A196L, Q36*+I40V+V150I+A196L, L37*+A78C+V150I+A196L, L37*+I90C+V150I+A196L, L37*+N114A+V150I+A196L, L37*+I40V+V150I+A196L, A78C+I90C+V150I+A196L, A78C+N114A+V150I+A196L, I40V+A78C+V150I+A196L, I90C+N114A+V150I+A196L, I40V+I90C+V150I+A196L, I40V+N114A+V150I+A196L, Q36*+L37*+A78C+V150I, Q36*+L37*+I90C+V150I, Q36*+L37*+N114A+V150I, Q36*+L37*+I40V+V150I, Q36*+A78C+I90C+V150I, Q36*+A78C+N114A+V150I, Q36*+I40V+A78C+V150I, Q36*+I90C+N114A+V150I, Q36*+I40V+I90C+V150I, Q36*+I40V+N114A+V150I, L37*+A78C+I90C+V150I, L37*+A78C+N114A+V150I, L37*+I40V+A78C+V150I, L37*+I90C+N114A+V150I, L37*+I40V+I90C+V150I, L37*+I40V+N114A+V150I, A78C+I90C+N114A+V150I, I40V+A78C+I90C+V150I, I40V+A78C+N114A+V150I, I40V+I90C+N114A+V150I, Q36*+L37*+A78C+A196L, Q36*+L37*+I90C+A196L, Q36*+L37*+N114A+A196L, Q36*+L37*+I40V+A196L, Q36*+A78C+I90C+A196L, Q36*+A78C+N114A+A196L, Q36*+I40V+A78C+A196L, Q36*+I90C+N114A+A196L, Q36*+I40V+I90C+A196L, Q36*+I40V+N114A+A196L, L37*+A78C+I90C+A196L, L37*+A78C+N114A+A196L, L37*+I40V+A78C+A196L, L37*+I90C+N114A+A196L, L37*+I40V+I90C+A196L, L37*+I40V+N114A+A196L, A78C+I90C+N114A+A196L, I40V+A78C+I90C+A196L, I40V+A78C+N114A+A196L, I40V+I90C+N114A+A196L, Q36*+L37*+A78C+I90C, Q36*+L37*+A78C+N114A, Q36*+L37*+I40V+A78C, Q36*+L37*+I90C+N114A, Q36*+L37*+I40V+I90C, Q36*+L37*+I40V+N114A, Q36*+A78C+I90C+N114A, Q36*+I40V+A78C+I90C, Q36*+I40V+A78C+N114A, Q36*+I40V+I90C+N114A, L37*+A78C+I90C+N114A, L37*+I40V+A78C+I90C, L37*+I40V+A78C+N114A, L37*+I40V+I90C+N114A, I40V+A78C+I90C+N114A of the mature polypeptide of SEQ ID NO: 2.

In another aspect, the variant comprises or consists of the substitutions Q36*+V150I+A196L+R216P+G217*, L37*+V150I+A196L+R216P+G217*, A78C+V150I+A196L+R216P+G217*, I90C+V150I+A196L+R216P+G217*, N114A+V150I+A196L+R216P+G217*, I40V+V150I+A196L+R216P+G217*, Q36*+L37*+V150I+R216P+G217*, Q36*+A78C+V150I+R216P+G217*, Q36*+I90C+V150I+R216P+G217*, Q36*+N114A+V150I+R216P+G217*, Q36*+I40V+V150I+R216P+G217*, L37*+A78C+V150I+R216P+G217*, L37*+I90C+V150I+R216P+G217*, L37*+N114A+V150I+R216P+G217*, L37*+I40V+V150I+R216P+G217*, A78C+I90C+V150I+R216P+G217*, A78C+N114A+V150I+R216P+G217*, I40V+A78C+V150I+R216P+G217*, I90C+N114A+V150I+R216P+G217*, I40V+I90C+V150I+R216P+G217*, I40V+N114A+V150I+R216P+G217*, Q36*+L37*+A196L+R216P+G217*, Q36*+A78C+A196L+R216P+G217*, Q36*+I90C+A196L+R216P+G217*, Q36*+N114A+A196L+R216P+G217*, Q36*+I40V+A196L+R216P+G217*, L37*+A78C+A196L+R216P+G217*, L37*+I90C+A196L+R216P+G217*, L37*+N114A+A196L+R216P+G217*, L37*+I40V+A196L+R216P+G217*, A78C+I90C+A196L+R216P+G217*, A78C+N114A+A196L+R216P+G217*, I40V+A78C+A196L+R216P+G217*, I90C+N114A+A196L+R216P+G217*, I40V+I90C+A196L+R216P+G217*, I40V+N114A+A196L+R216P+G217*, Q36*+L37*+A78C+R216P+G217*, Q36*+L37*+I90C+R216P+G217*, Q36*+L37*+N114A+R216P+G217*, Q36*+L37*+I40V+R216P+G217*, Q36*+A78C+I90C+R216P+G217*, Q36*+A78C+N114A+R216P+G217*, Q36*+I40V+A78C+R216P+G217*, Q36*+I90C+N114A+R216P+G217*, Q36*+I40V+I90C+R216P+G217*, Q36*+I40V+N114A+R216P+G217*, L37*+A78C+I90C+R216P+G217*, L37*+A78C+N114A+R216P+G217*, L37*+I40V+A78C+R216P+G217*, L37*+I90C+N114A+R216P+G217*, L37*+I40V+I90C+R216P+G217*, L37*+I40V+N114A+R216P+G217*, A78C+I90C+N114A+R216P+G217*, I40V+A78C+I90C+R216P+G217*, I40V+A78C+N114A+R216P+G217*, I40V+I90C+N114A+R216P+G217*, Q36*+L37*+V150I+A196L+R216P, Q36*+A78C+V150I+A196L+R216P, Q36*+I90C+V150I+A196L+R216P, Q36*+N114A+V150I+A196L+R216P, Q36*+I40V+V150I+A196L+R216P, L37*+A78C+V150I+A196L+R216P, L37*+I90C+V150I+A196L+R216P, L37*+N114A+V150I+A196L+R216P, L37*+I40V+V150I+A196L+R216P, A78C+I90C+V150I+A196L+R216P, A78C+N114A+V150I+A196L+R216P, I40V+A78C+V150I+A196L+R216P, I90C+N114A+V150I+A196L+R216P, I40V+I90C+V150I+A196L+R216P, I40V+N114A+V150I+A196L+R216P, Q36*+L37*+A78C+V150I+R216P, Q36*+L37*+I90C+V150I+R216P, Q36*+L37*+N114A+V150I+R216P, Q36*+L37*+I40V+V150I+R216P, Q36*+A78C+I90C+V150I+R216P, Q36*+A78C+N114A+V150I+R216P, Q36*+I40V+A78C+V150I+R216P, Q36*+I90C+N114A+V150I+R216P, Q36*+I40V+I90C+V150I+R216P, Q36*+I40V+N114A+V150I+R216P, L37*+A78C+I90C+V150I+R216P, L37*+A78C+N114A+V150I+R216P, L37*+I40V+A78C+V150I+R216P, L37*+I90C+N114A+V150I+R216P, L37*+I40V+I90C+V150I+R216P, L37*+I40V+N114A+V150I+R216P, A78C+I90C+N114A+V150I+R216P, I40V+A78C+I90C+V150I+R216P, I40V+A78C+N114A+V150I+R216P, I40V+I90C+N114A+V150I+R216P, Q36*+L37*+A78C+A196L+R216P, Q36*+L37*+I90C+A196L+R216P, Q36*+L37*+N114A+A196L+R216P, Q36*+A78C+I90C+A196L+R216P, Q36*+A78C+N114A+A196L+R216P, Q36*+I40V+A78C+A196L+R216P, Q36*+I90C+N114A+A196L+R216P, Q36*+I40V+I90C+A196L+R216P, Q36*+I40V+N114A+A196L+R216P, L37*+A78C+I90C+A196L+R216P, L37*+A78C+N114A+A196L+R216P, R216P, L37*+I40V+A78C+A196L+R216P, L37*+I90C+ N114A+A196L+R216P, L37*+I40V+I90C+A196L+R216P, L37*+I40V+N114A+A196L+R216P, A78C+I90C+ N114A+A196L+R216P, I40V+A78C+I90C+A196L+ R216P, I40V+A78C+N114A+A196L+R216P, I40V+I90C+ N114A+A196L+R216P, Q36*+L37*+A78C+I90C+R216P, Q36*+L37*+A78C+N114A+R216P, Q36*+L37*+I40V+ A78C+R216P, Q36*+L37*+I90C+N114A+R216P, Q36*+ L37*+I40V+I90C+R216P, Q36*+L37*+I40V+N114A+ R216P, Q36*+A78C+I90C+N114A+R216P, Q36*+I40V+ A78C+I90C+R216P, Q36*+I40V+A78C+N114A+R216P, Q36*+I40V+I90C+N114A+R216P, L37*+A78C+I90C+ N114A+R216P, L37*+I40V+A78C+I90C+R216P, L37*+ I40V+A78C+N114A+R216P, L37*+I40V+I90C+N114A+ R216P, I40V+A78C+I90C+N114A+R216P, Q36*+L37*+ V150I+A196L+G217*, Q36*+A78C+V150I+A196L+ G217*, Q36*+I90C+V150I+A196L+G217*, Q36*+ N114A+V150I+A196L+G217*, Q36*+I40V+V150I+ A196L+G217*, L37*+A78C+V150I+A196L+G217*, L37*+I90C+V150I+A196L+G217*, L37*+N114A+ V150I+A196L+G217*, L37*+I40V+V150I+A196L+ G217*, A78C+I90C+V150I+A196L+G217*, A78C+ N114A+V150I+A196L+G217*, I40V+A78C+V150I+ A196L+G217*, I90C+N114A+V150I+A196L+G217*, I40V+I90C+V150I+A196L+G217*, I40V+N114A+V150I+ A196L+G217*, Q36*+L37*+A78C+V150I+G217*, Q36*+ L37*+I90C+V150I+G217*, Q36*+L37*+N114A+V150I+ G217*, Q36*+L37*+I40V+V150I+G217*, Q36*+A78C+ I90C+V150I+G217*, Q36*+A78C+N114A+V150I+ G217*, Q36*+I40V+A78C+V150I+G217*, Q36*+I90C+ N114A+V150I+G217*, Q36*+I40V+I90C+V150I+G217*, Q36*+I40V+N114A+V150I+G217*, L37*+A78C+I90C+ V150I+G217*, L37*+A78C+N114A+V150I+G217*, L37*+I40V+A78C+V150I+G217*, L37*+I90C+N114A+ V150I+G217*, L37*+I40V+I90C+V150I+G217*, L37*+ I40V+N114A+V150I+G217*, A78C+I90C+N114A+ V150I+G217*, I40V+A78C+I90C+V150I+G217*, I40V+ A78C+N114A+V150I+G217*, I40V+I90C+N114A+ V150I+G217*, Q36*+L37*+A78C+A196L+G217*, Q36*+ L37*+I90C+A196L+G217*, Q36*+L37*+N114A+ A196L+G217*, Q36*+L37*+I40V+A196L+G217*, Q36*+ A78C+I90C+A196L+G217*, Q36*+A78C+N114A+ A196L+G217*, Q36*+I40V+A78C+A196L+G217*, Q36*+I90C+N114A+A196L+G217*, Q36*+I90C+V150I+ A196L+G217*, Q36*+I40V+N114A+A196L+G217*, L37*+A78C+I90C+A196L+G217*, L37*+A78C+N114A+ A196L+G217*, L37*+I40V+A78C+A196L+G217*, L37*+ I90C+N114A+A196L+G217*, L37*+I40V+I90C+A196L+ G217*, L37*+I40V+N114A+A196L+G217*, A78C+I90C+ N114A+A196L+G217*, I40V+A78C+I90C+A196L+ G217*, I40V+A78C+N114A+A196L+G217*, I40V+I90C+ N114A+A196L+G217*, Q36*+L37*+A78C+I90C+G217*, Q36*+L37*+A78C+N114A+G217*, Q36*+L37*+I40V+ A78C+G217*, Q36*+L37*+I90C+N114A+G217*, Q36*+ L37*+I40V+I90C+G217*, Q36*+L37*+I40V+N114A+ G217*, Q36*+A78C+I90C+N114A+G217*, Q36*+I40V+ A78C+I90C+G217*, Q36*+I40V+A78C+N114A+G217*, Q36*+I40V+I90C+N114A+G217*, L37*+A78C+I90C+ N114A+G217*, L37*+I40V+A78C+I90C+G217*, L37*+ I40V+A78C+N114A+G217*, L37*+I40V+I90C+N114A+ G217*, I40V+A78C+I90C+N114A+G217*, Q36*+L37*+ A78C+V150I+A196L, Q36*+L37*+I90C+V150I+A196L, Q36*+L37*+N114A+V150I+A196L, Q36*+L37*+I40V+ V150I+A196L, Q36*+A78C+I90C+V150I+A196L, Q36*+ A78C+N114A+V150I+A196L, Q36*+I40V+A78C+ V150I+A196L, Q36*+I90C+N114A+V150I+A196L, Q36*+I40V+I90C+V150I+A196L, Q36*+I40V+N114A+ V150I+A196L, L37*+A78C+I90C+V150I+A196L, L37*+ A78C+N114A+V150I+A196L, L37*+I40V+A78C+ V150I+A196L, L37*+I90C+N114A+V150I+A196L, L37*+I40V+I90C+V150I+A196L, L37*+I40V+N114A+ V150I+A196L, A78C+I90C+N114A+V150I+A196L, I40V+A78C+I90C+V150I+A196L, I40V+A78C+N114A+ V150I+A196L, I40V+I90C+N114A+V150I+A196L, Q36*+L37*+A78C+I90C+V150I, Q36*+L37*+A78C+ N114A+V150I, Q36*+L37*+I40V+A78C+V150I, Q36*+ L37*+I90C+N114A+V150I, Q36*+L37*+I40V+I90C+ V150I, Q36*+L37*+I40V+N114A+V150I, Q36*+A78C+ I90C+N114A+V150I, Q36*+I40V+A78C+I90C+V150I, Q36*+I40V+A78C+N114A+V150I, Q36*+I40V+I90C+ N114A+V150I, L37*+A78C+I90C+N114A+V150I, L37*+ I40V+A78C+I90C+V150I, L37*+I40V+A78C+N114A+ V150I, L37*+I40V+I90C+N114A+V150I, I40V+A78C+ I90C+N114A+V150I, Q36*+L37*+A78C+I90C+A196L, Q36*+L37*+A78C+N114A+A196L, Q36*+L37*+I40V+ A78C+A196L, Q36*+L37*+I90C+N114A+A196L, Q36*+ L37*+I40V+I90C+A196L, Q36*+L37*+I40V+N114A+ A196L, Q36*+A78C+I90C+N114A+A196L, Q36*+I40V+ A78C+I90C+A196L, Q36*+I40V+A78C+N114A+A196L, Q36*+I40V+I90C+N114A+A196L, L37*+A78C+I90C+ N114A+A196L, L37*+I40V+A78C+I90C+A196L, L37*+ I40V+A78C+N114A+A196L, L37*+I40V+I90C+N114A+ A196L, I40V+A78C+I90C+N114A+A196L, Q36*+L37*+ A78C+I90C+N114A, Q36*+L37*+I40V+A78C+I90C, Q36*+L37*+I40V+A78C+N114A, Q36*+L37*+I40V+ I90C+N114A, Q36*+I40V+A78C+I90C+N114A, L37*+ I40V+A78C+I90C+N114A of the mature polypeptide of SEQ ID NO: 2.

In another aspect, the variant comprises or consists of the substitutions Q36*+L37*+V150I+A196L+R216P+G217*, Q36*+A78C+V150I+A196L+R216P+G217*, Q36*+I90C+ V150I+A196L+R216P+G217*, Q36*+N114A+V150I+ A196L+R216P+G217*, Q36*+I40V+V150I+A196L+ R216P+G217*, L37*+A78C+V150I+A196L+R216P+ G217*, L37*+I90C+V150I+A196L+R216P+G217*, L37*+ N114A+V150I+A196L+R216P+G217*, L37*+I40V+ V150I+A196L+R216P+G217*, A78C+I90C+V150I+ A196L+R216P+G217*, A78C+N114A+V150I+A196L+ R216P+G217*, I40V+A78C+V150I+A196L+R216P+ G217*, I90C+N114A+V150I+A196L+R216P+G217*, I40V+I90C+V150I+A196L+R216P+G217*, I40V+ N114A+V150I+A196L+R216P+G217*, Q36*+L37*+ A78C+V150I+R216P+G217*, Q36*+L37*+I90C+V150I+ R216P+G217*, Q36*+L37*+N114A+V150I+R216P+ G217*, Q36*+L37*+I40V+V150I+R216P+G217*, Q36*+ A78C+I90C+V150I+R216P+G217*, Q36*+A78C+ N114A+V150I+R216P+G217*, Q36*+I40V+A78C+ V150I+R216P+G217*, Q36*+I90C+N114A+V150I+ R216P+G217*, Q36*+I40V+I90C+V150I+R216P+G217*, Q36*+I40V+N114A+V150I+R216P+G217*, L37*+A78C+ I90C+V150I+R216P+G217*, L37*+A78C+N114A+ V150I+R216P+G217*, L37*+I40V+A78C+V150I+ R216P+G217*, L37*+I90C+N114A+V150I+R216P+ G217*, L37*+I40V+I90C+V150I+R216P+G217*, L37*+ I40V+N114A+V150I+R216P+G217*, A78C+I90C+ N114A+V150I+R216P+G217*, I40V+A78C+I90C+ V150I+R216P+G217*, I40V+A78C+N114A+V150I+ R216P+G217*, I40V+I90C+N114A+V150I+R216P+ G217*, Q36*+L37*+A78C+A196L+R216P+G217*, Q36*+L37*+I90C+A196L+R216P+G217*, Q36*+L37*+ N114A+A196L+R216P+G217*, Q36*+L37*+ A196L+R216P+G217*, R216P+Q36*+A78C+I90C+ A196L+R216P+G217*, Q36*+A78C+N114A+A196L+ R216P+G217*, Q36*+I40V+A78C+A196L+R216P+

G217*, Q36*+I90C+N114A+A196L+R216P+G217*, Q36*+I40V+I90C+A196L+R216P+G217*, Q36*+I40V+N114A+A196L+R216P+G217*, L37*+A78C+I90C+A196L+R216P+G217*, L37*+A78C+N114A+A196L+R216P+G217*, L37*+I40V+A78C+A196L+R216P+G217*, L37*+I90C+N114A+A196L+R216P+G217*, L37*+I40V+I90C+A196L+R216P+G217*, L37*+I40V+N114A+A196L+R216P+G217*, A78C+I90C+N114A+A196L+R216P+G217*, I40V+A78C+I90C+A196L+R216P+G217*, I40V+A78C+N114A+A196L+R216P+G217*, I40V+I90C+N114A+A196L+R216P+G217*, Q36*+L37*+A78C+I90C+R216P+G217*, Q36*+L37*+A78C+N114A+R216P+G217*, Q36*+L37*+I40V+A78C+R216P+G217*, Q36*+L37*+I90C+N114A+R216P+G217*, Q36*+L37*+I40V+I90C+R216P+G217*, Q36*+L37*+I40V+N114A+R216P+G217*, Q36*+A78C+I90C+N114A+R216P+G217*, Q36*+I40V+A78C+I90C+R216P+G217*, Q36*+I40V+A78C+N114A+R216P+G217*, Q36*+I40V+I90C+N114A+R216P+G217*, L37*+A78C+I90C+N114A+R216P+G217*, L37*+I40V+A78C+I90C+R216P+G217*, L37*+I40V+A78C+N114A+R216P+G217*, L37*+I40V+I90C+N114A+R216P+G217*, I40V+A78C+I90C+N114A+R216P+G217*, Q36*+L37*+A78C+V150I+A196L+R216P, Q36*+L37*+I90C+V150I+A196L+R216P, Q36*+L37*+N114A+V150I+A196L+R216P, Q36*+L37*+I40V+V150I+A196L+R216P, Q36*+A78C+I90C+V150I+A196L+R216P, Q36*+A78C+N114A+V150I+A196L+R216P, Q36*+I40V+A78C+V150I+A196L+R216P, Q36*+I90C+N114A+V150I+A196L+R216P, Q36*+I40V+I90C+V150I+A196L+R216P, Q36*+I40V+N114A+V150I+A196L+R216P, L37*+A78C+I90C+V150I+A196L+R216P, L37*+A78C+N114A+V150I+A196L+R216P, L37*+I40V+A78C+V150I+A196L+R216P, L37*+I90C+N114A+V150I+A196L+R216P, L37*+I40V+I90C+V150I+A196L+R216P, L37*+I40V+N114A+V150I+A196L+R216P, A78C+I90C+N114A+V150I+A196L+R216P, I40V+A78C+I90C+V150I+A196L+R216P, I40V+A78C+N114A+V150I+A196L+R216P, I40V+I90C+N114A+V150I+A196L+R216P, Q36*+L37*+A78C+I90C+V150I+R216P, Q36*+L37*+A78C+N114A+V150I+R216P, Q36*+L37*+I40V+A78C+V150I+R216P, Q36*+L37*+I90C+N114A+V150I+R216P, Q36*+L37*+I40V+I90C+V150I+R216P, Q36*+L37*+I40V+N114A+V150I+R216P, Q36*+A78C+I90C+N114A+V150I+R216P, Q36*+I40V+A78C+I90C+V150I+R216P, Q36*+I40V+A78C+N114A+V150I+R216P, Q36*+I40V+I90C+N114A+V150I+R216P, L37*+A78C+I90C+N114A+V150I+R216P, L37*+I40V+A78C+I90C+V150I+R216P, L37*+I40V+A78C+N114A+V150I+R216P, L37*+I40V+I90C+N114A+V150I+R216P, I40V+A78C+I90C+N114A+V150I+R216P, Q36*+L37*+A78C+I90C+A196L+R216P, Q36*+L37*+A78C+N114A+A196L+R216P, Q36*+L37*+I40V+A78C+A196L+R216P, Q36*+L37*+I90C+N114A+A196L+R216P, Q36*+L37*+I40V+I90C+A196L+R216P, Q36*+L37*+I40V+N114A+A196L+R216P, Q36*+A78C+I90C+N114A+A196L+R216P, Q36*+I40V+A78C+I90C+A196L+R216P, Q36*+I40V+A78C+N114A+A196L+R216P, Q36*+I40V+I90C+N114A+A196L+R216P, L37*+A78C+I90C+N114A+A196L+R216P, L37*+I40V+A78C+I90C+A196L+R216P, L37*+I40V+A78C+N114A+A196L+R216P, L37*+I40V+I90C+N114A+A196L+R216P, I40V+A78C+I90C+N114A+A196L+R216P, Q36*+L37*+A78C+I90C+R216P, Q36*+L37*+I40V+A78C+N114A+R216P, Q36*+L37*+I40V+I90C+N114A+R216P, Q36*+I40V+A78C+I90C+N114A+R216P, L37*+I40V+A78C+I90C+N114A+R216P, Q36*+L37*+A78C+V150I+A196L+G217*, Q36*+L37*+I90C+V150I+A196L+G217*, Q36*+L37*+N114A+V150I+A196L+G217*, Q36*+L37*+I40V+V150I+A196L+G217*, Q36*+A78C+I90C+V150I+A196L+G217*, Q36*+A78C+N114A+V150I+A196L+G217*, Q36*+I40V+A78C+V150I+A196L+G217*, Q36*+I90C+N114A+V150I+A196L+G217*, Q36*+I40V+I90C+V150I+A196L+G217*, Q36*+I40V+N114A+V150I+A196L+G217*, L37*+A78C+I90C+V150I+A196L+G217*, L37*+A78C+N114A+V150I+A196L+G217*, L37*+I40V+A78C+V150I+A196L+G217*, L37*+I90C+N114A+V150I+A196L+G217*, L37*+I40V+I90C+V150I+A196L+G217*, L37*+I40V+N114A+V150I+A196L+G217*, A78C+I90C+N114A+V150I+A196L+G217*, I40V+A78C+I90C+V150I+A196L+G217*, I40V+A78C+N114A+V150I+A196L+G217*, I40V+I90C+N114A+V150I+A196L+G217*, Q36*+L37*+A78C+I90C+V150I+G217*, Q36*+L37*+A78C+N114A+V150I+G217*, Q36*+L37*+I40V+A78C+V150I+G217*, Q36*+L37*+I90C+N114A+V150I+G217*, Q36*+L37*+I40V+I90C+V150I+G217*, Q36*+L37*+I40V+N114A+V150I+G217*, Q36*+A78C+I90C+N114A+V150I+G217*, Q36*+I40V+A78C+I90C+V150I+G217*, Q36*+I40V+A78C+N114A+V150I+G217*, Q36*+I40V+I90C+N114A+V150I+G217*, L37*+A78C+I90C+N114A+V150I+G217*, L37*+I40V+A78C+I90C+V150I+G217*, L37*+I40V+A78C+N114A+V150I+G217*, L37*+I40V+I90C+N114A+V150I+G217*, I40V+A78C+I90C+N114A+V150I+G217*, Q36*+L37*+A78C+I90C+A196L+G217*, Q36*+L37*+A78C+N114A+A196L+G217*, Q36*+L37*+I40V+A78C+A196L+G217*, Q36*+L37*+I90C+N114A+A196L+G217*, Q36*+L37*+I40V+I90C+A196L+G217*, Q36*+L37*+I40V+N114A+A196L+G217*, Q36*+A78C+I90C+N114A+A196L+G217*, Q36*+I40V+A78C+I90C+A196L+G217*, Q36*+I40V+A78C+N114A+A196L+G217*, Q36*+I40V+I90C+N114A+A196L+G217*, L37*+A78C+I90C+N114A+A196L+G217*, L37*+I40V+A78C+I90C+A196L+G217*, L37*+I40V+A78C+N114A+A196L+G217*, L37*+I40V+I90C+N114A+A196L+G217*, I40V+A78C+I90C+N114A+A196L+G217*, Q36*+L37*+A78C+I90C+N114A+G217*, Q36*+L37*+I40V+A78C+I90C+G217*, Q36*+L37*+I40V+A78C+N114A+G217*, Q36*+L37*+I40V+I90C+N114A+G217*, Q36*+I40V+A78C+I90C+N114A+G217*, L37*+I40V+A78C+I90C+N114A+G217*, Q36*+L37*+A78C+I90C+V150I+A196L, Q36*+L37*+A78C+N114A+V150I+A196L, Q36*+L37*+I40V+A78C+V150I+A196L, Q36*+L37*+I90C+N114A+V150I+A196L, Q36*+L37*+I40V+I90C+V150I+A196L, Q36*+L37*+I40V+N114A+V150I+A196L, Q36*+A78C+I90C+N114A+V150I+A196L, Q36*+I40V+A78C+I90C+V150I+A196L, Q36*+I40V+A78C+N114A+V150I+A196L, Q36*+I40V+I90C+N114A+V150I+A196L, L37*+A78C+I90C+N114A+V150I+A196L, L37*+I40V+A78C+I90C+V150I+A196L, L37*+I40V+A78C+N114A+V150I+A196L, L37*+I40V+I90C+N114A+V150I+A196L, I40V+A78C+I90C+N114A+V150I+A196L, Q36*+L37*+A78C+I90C+N114A+V150I+V150I0, Q36*+L37*+I40V+A78C+I90C+V150I, Q36*+L37*+I40V+A78C+N114A+V150I, Q36*+L37*+I40V+I90C+N114A+V150I, Q36*+I40V+A78C+I90C+N114A+V150I, L37*+I40V+A78C+I90C+N114A+V150I, Q36*+L37*+A78C+I90C+N114A+A196L, Q36*+L37*+I40V+A78C+I90C+A196L, Q36*+L37*+I40V+A78C+N114A+A196L, Q36*+L37*+I40V+I90C+N114A+A196L, Q36*+I40V+A78C+I90C+N114A+A196L, L37*+I40V+A78C+I90C+N114A+A196L, Q36*+L37*+I40V+A78C+I90C+N114A of the mature polypeptide of SEQ ID NO: 2.

In another aspect, the variant comprises or consists of the substitutions Q36*+L37*+A78C+V150I+A196L+R216P+G217*, Q36*+L37*+I90C+V150I+A196L+R216P+G217*, Q36*+L37*+N114A+V150I+A196L+R216P+G217*, Q36*+L37*+I40V+V150I+A196L+R216P+G217*, Q36*+A78C+I90C+V150I+A196L+R216P+G217*, Q36*+A78C+N114A+V150I+A196L+R216P+G217*, Q36*+I40V+A78C+V150I+A196L+R216P+G217*, Q36*+I90C+N114A+V150I+A196L+R216P+G217*, Q36*+I40V+I90C+V150I+A196L+R216P+G217*, I40V+N114A+V150I+A196L+R216P+G217*, L37*+A78C+I90C+V150I+A196L+R216P+G217*, L37*+A78C+N114A+V150I+A196L+R216P+G217*, L37*+I40V+A78C+V150I+A196L+R216P+G217*, L37*+I90C+N114A+V150I+A196L+R216P+G217*, L37*+I40V+I90C+V150I+A196L+R216P+G217*, L37*+I40V+N114A+V150I+A196L+R216P+G217*, A78C+I90C+N114A+V150I+A196L+R216P+G217*, I40V+A78C+I90C+V150I+A196L+R216P+G217*, I40V+A78C+N114A+V150I+A196L+R216P+G217*, I40V+I90C+N114A+V150I+A196L+R216P+G217*, Q36*+L37*+A78C+I90C+V150I+R216P+G217*, Q36*+L37*+A78C+N114A+V150I+R216P+G217*, Q36*+L37*+I40V+A78C+V150I+R216P+G217*, Q36*+L37*+I90C+N114A+V150I+R216P+G217*, Q36*+L37*+I40V+I90C+V150I+R216P+G217*, Q36*+L37*+I40V+N114A+V150I+R216P+G217*, Q36*+A78C+I90C+N114A+V150I+R216P+G217*, Q36*+I40V+A78C+I90C+V150I+R216P+G217*, Q36*+I40V+A78C+N114A+V150I+R216P+G217*, Q36*+I40V+I90C+N114A+V150I+R216P+G217*, L37*+A78C+I90C+N114A+V150I+R216P+G217*, L37*+I40V+A78C+I90C+V150I+R216P+G217*, L37*+I40V+A78C+N114A+V150I+R216P+G217*, L37*+I40V+I90C+N114A+V150I+R216P+G217*, I40V+A78C+I90C+N114A+V150I+R216P+G217*, Q36*+L37*+A78C+I90C+A196L+R216P+G217*, Q36*+L37*+A78C+N114A+A196L+R216P+G217*, Q36*+L37*+I40V+A78C+A196L+R216P+G217*, Q36*+L37*+I90C+N114A+A196L+R216P+G217*, Q36*+L37*+I40V+I90C+A196L+R216P+G217*, Q36*+L37*+I40V+N114A+A196L+R216P+G217*, Q36*+A78C+I90C+N114A+A196L+R216P+G217*, Q36*+I40V+A78C+I90C+A196L+R216P+G217*, Q36*+I40V+A78C+N114A+A196L+R216P+G217*, Q36*+I40V+I90C+N114A+A196L+R216P+G217*, L37*+A78C+I90C+N114A+A196L+R216P+G217*, L37*+I40V+A78C+I90C+A196L+R216P+G217*, L37*+I40V+A78C+N114A+A196L+R216P+G217*, L37*+I40V+I90C+N114A+A196L+R216P+G217*, I40V+A78C+I90C+N114A+A196L+R216P+G217*, Q36*+L37*+A78C+I90C+N114A+R216P+G217*, Q36*+L37*+I40V+A78C+I90C+R216P+G217*, Q36*+L37*+I40V+A78C+N114A+R216P+G217*, Q36*+L37*+I40V+I90C+N114A+R216P+G217*, Q36*+I40V+A78C+I90C+N114A+R216P+G217*, L37*+I40V+A78C+I90C+N114A+R216P+G217*, Q36*+L37*+A78C+I90C+V150I+A196L+R216P, Q36*+L37*+A78C+N114A+V150I+A196L+R216P, Q36*+L37*+I40V+A78C+V150I+A196L+R216P, Q36*+L37*+I90C+N114A+V150I+A196L+R216P, Q36*+L37*+I40V+I90C+V150I+A196L+R216P, Q36*+L37*+I40V+N114A+V150I+A196L+R216P, Q36*+A78C+I90C+N114A+V150I+A196L+R216P, Q36*+I40V+A78C+I90C+V150I+A196L+R216P, Q36*+I40V+A78C+N114A+V150I+A196L+R216P, Q36*+I40V+I90C+N114A+V150I+A196L+R216P, L37*+A78C+I90C+N114A+V150I+A196L+R216P, L37*+I40V+A78C+I90C+V150I+A196L+R216P, L37*+I40V+A78C+N114A+V150I+A196L+R216P, L37*+I40V+I90C+N114A+V150I+A196L+R216P, I40V+A78C+I90C+N114A+V150I+A196L+R216P, Q36*+L37*+A78C+I90C+N114A+V150I+R216P, Q36*+L37*+I40V+A78C+I90C+V150I+R216P, Q36*+L37*+I40V+A78C+N114A+V150I+R216P, Q36*+L37*+I40V+I90C+N114A+V150I+R216P, Q36*+I40V+A78C+I90C+N114A+V150I+R216P, L37*+I40V+A78C+I90C+N114A+V150I+R216P, Q36*+L37*+A78C+I90C+N114A+A196L+R216P, Q36*+L37*+I40V+A78C+I90C+A196L+R216P, Q36*+L37*+I40V+A78C+N114A+A196L+R216P, Q36*+L37*+I40V+I90C+N114A+A196L+R216P, Q36*+I40V+A78C+I90C+N114A+A196L+R216P, L37*+I40V+A78C+I90C+N114A+A196L+R216P, Q36*+L37*+I40V+A78C+I90C+N114A+R216P, Q36*+L37*+A78C+I90C+V150I+A196L+G217*, Q36*+L37*+A78C+N114A+V150I+A196L+G217*, Q36*+L37*+I40V+A78C+V150I+A196L+G217*, Q36*+L37*+I90C+N114A+V150I+A196L+G217*, Q36*+L37*+I40V+I90C+V150I+A196L+G217*, Q36*+L37*+I40V+N114A+V150I+A196L+G217*, Q36*+A78C+I90C+N114A+V150I+A196L+G217*, Q36*+I40V+A78C+I90C+V150I+A196L+G217*, Q36*+I40V+A78C+N114A+V150I+A196L+G217*, Q36*+I40V+I90C+N114A+V150I+A196L+G217*, L37*+A78C+I90C+N114A+V150I+A196L+G217*, L37*+I40V+A78C+I90C+V150I+A196L+G217*, L37*+I40V+A78C+N114A+V150I+A196L+G217*, L37*+I40V+I90C+N114A+V150I+A196L+G217*, I40V+A78C+I90C+N114A+V150I+A196L+G217*, Q36*+L37*+A78C+I90C+N114A+V150I+G217*, Q36*+L37*+I40V+A78C+I90C+V150I+G217*, Q36*+L37*+I40V+A78C+N114A+V150I+G217*, Q36*+L37*+I40V+I90C+N114A+V150I+G217*, Q36*+I40V+A78C+I90C+N114A+V150I+G217*, L37*+I40V+A78C+I90C+N114A+V150I+G217*, Q36*+L37*+A78C+I90C+N114A+A196L+G217*, Q36*+L37*+I40V+A78C+I90C+A196L+G217*, Q36*+L37*+I40V+A78C+N114A+A196L+G217*, Q36*+L37*+I40V+I90C+N114A+A196L+G217*, Q36*+I40V+A78C+I90C+N114A+A196L+G217*, L37*+I40V+A78C+I90C+N114A+A196L+G217*, Q36*+L37*+I40V+A78C+I90C+N114A+G217*, Q36*+L37*+A78C+I90C+N114A+V150I+A196L, Q36*+L37*+I40V+A78C+I90C+V150I+A196L, Q36*+L37*+I40V+A78C+N114A+V150I+A196L, Q36*+L37*+I40V+I90C+N114A+V150I+A196L, Q36*+I40V+A78C+I90C+N114A+V150I+A196L, L37*+I40V+A78C+I90C+N114A+V150I+A196L, Q36*+L37*+I40V+A78C+I90C+N114A+V150I, Q36*+L37*+I40V+A78C+I90C+N114A+A196L of the mature polypeptide of SEQ ID NO: 2.

In another aspect, the variant comprises or consists of the substitutions Q36*+L37*+A78C+I90C+V150I+A196L+R216P+G217*, Q36*+L37*+A78C+N114A+V150I+A196L+R216P+G217*, Q36*+L37*+I40V+A78C+V150I+A196L+R216P+G217*, Q36*+L37*+I90C+N114A+V150I+A196L+R216P+G217*, Q36*+L37*+I40V+I90C+V150I+A196L+R216P+G217*, Q36*+L37*+I40V+N114A+V150I+A196L+R216P+G217*, Q36*+A78C+I90C+N114A+V150I+A196L+R216P+G217*, Q36*+I40V+A78C+I90C+V150I+A196L+R216P+G217*, Q36*+I40V+A78C+N114A+V150I+A196L+R216P+G217*, Q36*+I40V+I90C+N114A+V150I+A196L+R216P+G217*, L37*+A78C+I90C+N114A+V150I+A196L+R216P+G217*, L37*+I40V+A78C+I90C+V150I+A196L+R216P+G217*, L37*+I40V+A78C+N114A+V150I+A196L+R216P+G217*, L37*+I40V+I90C+N114A+V150I+A196L+R216P+G217*, I40V+A78C+I90C+N114A+V150I+A196L+R216P+G217*, Q36*+L37*+A78C+I90C+N114A+V150I+R216P+G217*, Q36*+L37*+I40V+A78C+I90C+V150I+R216P+G217*, Q36*+L37*+I40V+A78C+N114A+V150I+R216P+G217*, Q36*+L37*+

I40V+I90C+N114A+V150I+R216P+G217*, Q36*+I40V+ A78C+I90C+N114A+V150I+R216P+G217*, L37*+I40V+ A78C+I90C+N114A+V150I+R216P+G217*, Q36*+L37*+ A78C+I90C+N114A+A196L+R216P+G217*, Q36*+ L37*+I40V+A78C+I90C+A196L+R216P+G217*, Q36*+ L37*+I40V+A78C+N114A+A196L+R216P+G217*, Q36*+L37*+I40V+I90C+N114A+A196L+R216P+G217*, Q36*+I40V+A78C+I90C+N114A+A196L+R216P+G217*, L37*+I40V+A78C+I90C+N114A+A196L+R216P+G217*, Q36*+L37*+I40V+A78C+I90C+N114A+R216P+G217*, Q36*+L37*+A78C+I90C+N114A+V150I+A196L+R216P, Q36*+L37*+I40V+A78C+I90C+V150I+A196L+R216P, Q36*+L37*+I40V+A78C+N114A+V150I+A196L+R216P, Q36*+L37*+I40V+I90C+N114A+V150I+A196L+R216P, Q36*+I40V+A78C+I90C+N114A+V150I+A196L+R216P, L37*+I40V+A78C+I90C+N114A+V150I+A196L+R216P, Q36*+L37*+I40V+A78C+I90C+N114A+V150I+R216P, Q36*+L37*+I40V+A78C+I90C+N114A+A196L+R216P, Q36*+L37*+A78C+I90C+N114A+V150I+A196L+G217*, Q36*+L37*+I40V+A78C+I90C+V150I+A196L+G217*, Q36*+L37*+I40V+A78C+N114A+V150I+A196L+G217*, Q36*+L37*+I40V+I90C+N114A+V150I+A196L+G217*, Q36*+I40V+A78C+I90C+N114A+V150I+A196L+G217*, L37*+I40V+A78C+I90C+N114A+V150I+A196L+G217*, Q36*+L37*+I40V+A78C+I90C+N114A+V150I+G217*, Q36*+L37*+I40V+A78C+I90C+N114A+A196L+G217*, Q36*+L37*+I40V+A78C+I90C+N114A+V150I+A196L of the mature polypeptide of SEQ ID NO: 2.

In another aspect, the variant comprises or consists of the Q36*+L37*+A78C+I90C+N114A+V150I+A196L+ R216P+G217*, Q36*+L37*+I40V+A78C+I90C+V150I+ A196L+R216P+G217*, Q36*+L37*+I40V+A78C+ N114A+V150I+A196L+R216P+G217*, Q36*+L37*+ I40V+I90C+N114A+V150I+A196L+R216P+G217*, Q36*+I40V+A78C+I90C+N114A+V150I+A196L+ R216P+G217*, L37*+I40V+A78C+I90C+N114A+V150I+ A196L+R216P+G217*, Q36*+L37*+I40V+A78C+I90C+ N114A+V150I+R216P+G217*, Q36*+L37*+I40V+A78C+ I90C+N114A+A196L+R216P+G217*, Q36*+L37*+I40V+ A78C+I90C+N114A+V150I+A196L+R216P, Q36*+L37*+ I40V+A78C+I90C+N114A+V150I+A196L+G217* of the mature polypeptide of SEQ ID NO: 2.

In another aspect, the variant comprises or consists of the substitutions Q36*+L37*+I40V+A78C+I90C+N114A+ V150I+A196L+R216P+G217* of the mature polypeptide of SEQ ID NO: 2.

The variants may further comprise one or more additional alterations at one or more (e.g., several) other positions.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for cutinase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

In one aspect, a variant may consist of or comprise at least 172 amino acid residues (e.g., amino acids 52 to 223 of SEQ ID NO: 2). In one aspect, the variant comprises at least 80%, at least 85%, at least 90%, at least 91%, at least 92%, at least 93%, at least 94%, at least 95%, at least 96%, at least 97%, at least 98%, or at least 99%, but less than 100% of the number of amino acids of SEQ ID No: 2. In one aspect, the variant comprises at least 172 amino acid residues (e.g., amino acids 52 to 223 of SEQ ID NO: 2) and at least 80%, at least 85%, at least 90%, at least 91%, at least 92%, at least 93%, at least 94%, at least 95%, at least 96%, at least 97%, at least 98%, or at least 99%, but less than 100% of the number of amino acids of SEQ ID No: 2.

In some aspects the invention relates to variants comprising an N-terminal extension. The extension may constitute positions corresponding amino acids to 19 to 35 of SEQ ID NO: 2 or truncations thereof. In some aspects the invention relates to a variant wherein the N-terminal extension is selected from: (a) AAVDSNHTPAVPELVAR (SEQ ID NO: 3); (b) AVDSNHTPAVPELVAR (SEQ ID NO: 4); (c) VDSNHTPAVPELVAR (SEQ ID NO: 5); (d) DSNHTPAVPELVAR (SEQ ID NO: 6); (e) SNHTPAVPELVAR (SEQ ID NO: 7); (f) NHTPAVPELVAR (SEQ ID NO: 8); (g) HTPAVPELVAR (SEQ ID NO: 9); (h) TPAVPELVAR (SEQ ID NO: 10); (i) PAVPELVAR (SEQ ID NO: 11); (j) AVPELVAR (SEQ ID NO: 12); (k) VPELVAR (SEQ ID NO: 13); (l) PELVAR (SEQ ID NO: 14); (m) ELVAR (SEQ ID NO: 15); (n) LVAR (SEQ ID NO: 16); (o) VAR; (p) AR; or (q) R. The variants comprising a deletion in one or more (e.g. several) of the positions corresponding to amino acid 36 and/or 37 of SEQ ID NO: 2 (e.g. Q36*, L37*, or Q36* and L37*) may have a different processing of the pro-region. This may in some aspects of the invention result in variants that have both a deletion in one or more (e.g. several) of the positions corresponding to amino acid 36 and/or 37 of SEQ ID NO: 2 (e.g. Q36*, L37*, or Q36* and L37*) and an N-terminal extension selected from: (a) AAVDSNHT-PAVPELVAR (SEQ ID NO: 3); (b) AVDSNHTPAVPELVAR (SEQ ID NO: 4); (c) VDSNHTPAVPELVAR (SEQ ID NO: 5); (d) DSNHTPAVPELVAR (SEQ ID NO: 6); (e) SNHTPAVPELVAR (SEQ ID NO: 7); (f) NHTPAVPELVAR (SEQ ID NO: 8); (g) HTPAVPELVAR (SEQ ID NO: 9); (h) TPAVPELVAR (SEQ ID NO: 10); (i) PAVPELVAR (SEQ ID NO: 11); (j) AVPELVAR (SEQ ID NO: 12); (k) VPELVAR (SEQ ID NO: 13); (l) PELVAR (SEQ ID NO: 14); (m) ELVAR (SEQ ID NO: 15); (n) LVAR (SEQ ID NO: 16); (o) VAR; (p) AR; or (q) R.

In one aspect, the variant has improved specific activity as compared to the parent enzyme. Specific activity may be determined by hydrolysis of BETEB as described in Example 3, and/or determined by increase of pH change and/or OD change by hydrolysis of PET as described in Example 4.

In one aspect, the variant has improved substrate binding as compared to the parent enzyme.

In one aspect, the variant has improved substrate cleavage as compared to the parent enzyme. Substrate cleavage may be determined by hydrolysis of BETEB as described in Example 3, and/or determined by increase of pH change and/or OD change by hydrolysis of PET as described in Example 4.

In one aspect, the variant has improved substrate specificity as compared to the parent enzyme. Substrate specificity may be determined by hydrolysis of BETEB as described in Example 3, and/or determined by increase of pH change and/or OD change by hydrolysis of PET as described in Example 4.

In one aspect, the variant has improved thermostability as compared to the parent enzyme. Thermostability may be determined by Differential Scanning calorimetry (DSC) or by determining the residual activity after incubation at a specified temperature as measured by hydrolysis of BETEB as described in Example 3, and/or determined by increase of pH change and/or OD change by hydrolysis of PET as described in Example 4.

Thermostability determined by Differential Scanning calorimetry (DSC) is conducted by using a VP-Capillary Differential Scanning calorimeter (MicroCal Inc., Piscataway, N.J., USA). The thermal denaturation temperature, Td (° C.), is taken as the top of denaturation peak (major endothermic peak) in thermograms (Cp vs. T) obtained after heating enzyme solutions (approx. 0.5 mg/mL) in buffer (50 mM Tris 100 mM NaCl pH9) at a constant programmed heating rate of 200K/hr. Sample- and reference-solutions (approx. 0.2 mL) is loaded into the calorimeter (reference: buffer without enzyme) from storage conditions at 10° C. and thermally pre-equilibrated for 20 minutes at 20° C. prior to DSC scan from 20° C. to 100° C. Denaturation temperature is determined at an accuracy of +/−1° C.

In one aspect, the variant has decreased pilling propensity as compared to the parent enzyme. Pilling propensity may be determined by conducting the Pilling Note Test as described in Example 4.

Parent Cutinases

The parent cutinase may be (a) a polypeptide having at least 60% sequence identity to the mature polypeptide of SEQ ID NO: 2; (b) a polypeptide encoded by a polynucleotide that hybridizes under low stringency conditions with the mature polypeptide coding sequence of SEQ ID NO: 1, or the full-length complement thereof; or (c) a polypeptide encoded by a polynucleotide having at least 60% sequence identity to the mature polypeptide coding sequence of SEQ ID NO: 1.

In an aspect, the parent has a sequence identity to the mature polypeptide of SEQ ID NO: 2 of at least 75%, at least 80%, at least 85%, at least 90%, at least 91%, at least 92%, at least 93%, at least 94%, at least 95%, at least 96%, at least 97%, at least 98%, at least 99%, or 100%, which have cutinase activity. In one aspect, the amino acid sequence of the parent differs by up to 20 amino acids, e.g., 1-15, 1-10, 1-5, 1, 2, 3, 4, 5, 6, 7, 8, 9, 10, 11, 12, 13, 14, 15, 16, 17, 18, 19, or 20 from the mature polypeptide of SEQ ID NO: 2.

In another aspect, the parent comprises or consists of the amino acid sequence of SEQ ID NO: 2. In another aspect, the parent comprises or consists of the mature polypeptide of SEQ ID NO: 2. In another aspect, the parent comprises or consists of amino acids 36 to 229 of SEQ ID NO: 2.

In another aspect, the parent is a fragment of the mature polypeptide of SEQ ID NO: 2 which consists or comprises at least 172 amino acid residues (e.g., corresponding to amino acids 52 to 223 of SEQ ID NO: 2). In one aspect, a fragment comprises at least 80%, at least 85%, at least 90%, at least 91%, at least 92%, at least 93%, at least 94%, at least 95%, at least 96%, at least 97%, at least 98%, or at least 99%, but less than 100% of the number of amino acids of SEQ ID No: 2. In one aspect, a fragment comprises at least 172 amino acid residues (e.g., amino acids 52 to 223 of SEQ ID NO: 2) and at least 80%, at least 85%, at least 90%, at least 91%, at least 92%, at least 93%, at least 94%, at least 95%, at least 96%, at least 97%, at least 98%, or at least 99%, but less than 100% of the number of amino acids of SEQ ID NO: 2.

In another aspect, the parent is an allelic variant of the mature polypeptide of SEQ ID NO: 2.

In another aspect, the parent is encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1 or the full-length complement thereof (Sambrook et al., 1989, *Molecular Cloning, A Laboratory Manual*, 2d edition, Cold Spring Harbor, New York).

The polynucleotide of SEQ ID NO: 1 or a subsequence thereof, as well as the polypeptide of SEQ ID NO: 2 or a fragment thereof, may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) SEQ ID NO: 1; (ii) the mature polypeptide coding sequence of SEQ ID NO: 1; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1. In another aspect, the nucleic acid probe is nucleotides 106 to 687 of SEQ ID NO: 1. In another aspect, the nucleic acid probe is a polynucleotide that encodes the polypeptide of SEQ ID NO: 2; the mature polypeptide thereof; or a fragment thereof. In another aspect, the nucleic acid probe is SEQ ID NO: 1.

In one aspect, the parent is encoded by a polynucleotide having a sequence identity to the mature polypeptide coding sequence of SEQ ID NO: 1 of at least 75%, at least 80%, at least 85%, at least 90%, at least 91%, at least 92%, at least 93%, at least 94%, at least 95%, at least 96%, at least 97%, at least 98%, at least 99%, or 100%.

The polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a bacterial cutinase. For example, the parent may be a Gram-positive bacterial polypeptide such as a *Bacillus*, *Clostridium*, *Enterococcus*, *Geobacillus*, *Lactobacillus*, *Lactococcus*, *Oceanobacillus*, *Staphylococcus*, *Streptococcus*, or *Streptomyces* cutinase, or a Gram-negative bacterial polypeptide such as a *Campylobacter*, *E. coli*, *Flavobacterium*, *Fusobacterium*, *Helicobacter*, *Ilyobacter*, *Neisseria*, *Pseudomonas*, *Salmonella*, or *Ureaplasma* cutinase.

In one aspect, the parent is a *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* cutinase.

In another aspect, the parent is a *Streptococcus equisimilis*, *Streptococcus pyogenes*, *Streptococcus uberis*, or *Streptococcus equi* subsp. *Zooepidemicus* cutinase.

In another aspect, the parent is a *Streptomyces achromogenes*, *Streptomyces avermitilis*, *Streptomyces coelicolor*, *Streptomyces griseus*, or *Streptomyces lividans* cutinase.

The parent may be a fungal cutinase. For example, the parent may be a yeast cutinase such as a *Candida*, *Kluyveromyces*, *Pichia*, *Saccharomyces*, *Schizosaccharomyces*, or *Yarrowia* cutinase; or a filamentous fungal cutinase such as an *Acremonium*, *Agaricus*, *Alternaria*, *Aspergillus*, *Aureobasidium*, *Botryosphaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Diplodia*, *Exidia*, *Filibasidium*, *Fusarium*, *Gibberella*, *Holomastigotoides*, *Humicola*, *Irpex*, *Lentinula*, *Leptospaeria*, *Magnaporthe*, *Melanocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvariella*, or *Xylaria* cutinase.

In another aspect, the parent is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* cutinase.

In another aspect, the parent is an *Acremonium cellulolyticus*, *Aspergillus aculeatus*, *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola grisea*, *Humicola insolens*, *Humicola lanuginosa*, *Irpex lacteus*, *Mucor miehei*, *Myceliophthora thermophila*, *Neurospora crassa*, *Penicillium funiculosum*, *Penicillium purpurogenum*, *Phanerochaete chrysosporium*, *Thielavia achromatica*, *Thielavia albomyces*, *Thielavia albopilosa*, *Thielavia australeinsis*, *Thielavia fimeti*, *Thielavia microspora*, *Thielavia ovispora*, *Thielavia peruviana*, *Thielavia setosa*, *Thielavia spededonium*, *Thielavia subthermophila*, *Thielavia terrestris, Trichoderma harzianum, Trichoderma koningii, Trichoderma longibrachiatum, Trichoderma reesei, or Trichoderma viride cutinase.

In another aspect, the parent is a Humicola insolens cutinase, or the cutinase of SEQ ID NO: 2 or the mature polypeptide thereof. In another aspect the parent may be a strain of Rhizoctonia, e.g. R. solani, or a strain of Alternaria, e.g. A. brassicicola (WO94/03578). The cutinase enzyme may also be a variant of a parent cutinase such as those described in WO00/34450, or WO01/92502.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to methods for obtaining a variant having cutinase activity, comprising: (a) introducing into a parent cutinase an alteration at one or more (e.g., several) positions corresponding to positions 36, 37, 40, 78, 90, 114, 150, 196, 216, or 217 of the mature polypeptide of SEQ ID NO: 2, wherein the alteration is a substitution for positions 40, 78, 90, 114, 150, 196 and 216, and a deletion for positions 36, 37 and 217, wherein the variant has at least 75%, at least 80%, at least 85%, at least 90%, at least 95%, at least 96%, at least 97%, at least 98%, or at least 99%, but less than 100% sequence identity to the mature polypeptide of SEQ ID NO: 2, and wherein the variant has cutinase activity; and (b) recovering the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, Proc. Natl. Acad. Sci. USA 76: 4949-4955; and Barton et al., 1990, Nucleic Acids Res. 18: 7349-4966.

Site-directed mutagenesis can also be accomplished in vivo by methods known in the art. See, e.g., US2004/0171154; Storici et al., 2001, Nature Biotechnol. 19: 773-776; Kren et al., 1998, Nat. Med. 4: 285-290; and Calissano and Macino, 1996, Fungal Genet. Newslett. 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, Nature 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO95/17413; or WO95/22625. Other methods that can be used include error-prone PCR, phage display (e.g., Lowman et al., 1991, Biochemistry 30: 10832-10837; U.S. Pat. No. 5,223,409; WO92/06204) and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector.

The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* crylllA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO96/00787), *Fusarium venenatum* amyloglucosidase (WO00/56900), *Fusarium venenatum* Dania (WO00/56900), *Fusarium venenatum* Quinn (WO00/56900), *Rhizomucor miehei* cutinase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* crylllA gene (WO94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* cutinase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (npr7), *Myceliophthora thermophila* laccase (WO95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., *In*,

*Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series No.* 9, 1980).

The yeast host cell may be a *Candida, Hansenula, Kluyveromyces, Pichia, Saccharomyces, Schizosaccharomyces,* or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium suiphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phiebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising: (a) cultivating a host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant. The cutinase activity may be determined as hydrolytic activity towards BETEB substrate as described in example 3.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Compositions

In some aspects the invention also relates to compositions comprising one or more (e.g. several) of the variants.

Uses

The cutinase variant of the invention may be used, e.g., for the enzymatic hydrolysis of cyclic oligomers of poly (ethylene terephthalate), such as cyclic tri(ethylene terephthalate), abbreviated as c3ET. They may be used to remove such cyclic oligomers from polyester containing fabric or yarn by treating the fabric or yarn with the cutinase variant, optionally followed by rinsing the fabric or yarn with an aqueous solution having a pH in the range of from pH 7 to pH 11. The treatment of polyester is conveniently carried out above the glass transition temperature of c3ET (about 55° C.) and below the glass transition temperature of polyester (about 70° C.). Thus, the treatment may suitably be carried out at 50-100° C., 50-95, 50-90° C., 50-85° C., 50-80° C., or 60-75° C. The process may be carried out in analogy with WO97/27237.

The cutinase variant may be used to treat textile/fabric consisting or comprising polyester, such as e.g. PET (polymer of ethyleneglycol and terephthalic acid), P3GT (polymer of 1,3-propanediol and terephthalic acid) or any blends thereof. Such polyester blends may e.g. comprise cotton (polyester/cotton blends) and/or other suitable fibres. The treatment may provide benefits to the textile/fabric consisting or comprising polyester such as reducing the pilling propensity.

The cutinase variant may be used to improve the functional finish of a PET-containing yarn or fabric by a treatment with the cutinase variant, followed by a treatment with a finishing agent such as a softener, an anti-crease resin, an anti-static agent, an anti-soiling agent or agents to impair wrinkle-free, permanent press or fire resistance effects. The treatment with the cutinase variant may increase the number of functional groups in the surface, and this can be used to attach the functional finish. Examples of finishing agents are described in "SENSHOKU SIAGEKAKO BENRAN" published 1998 Oct. 15 by Nihon Seni Sentaa KK.

The cutinase variant may also be used for degradation and recycling of polyester such as polycaprolactone (PCL), poly-ethyleneglycol-terephthalate (PET), polylactic acid, polybutylenesuccinate, and poly(hydroxybutiric acid)-co-(hydroxyvaleric acid), e.g. film and bottles, e.g. as described in JP-A 5-344897.

In some aspects the invention relates to a method for modifying polyester comprising use of one or more (e.g. several) of the variants.

In some aspects the invention relates to a method for hydrolyzing cyclic oligomers of poly(ethylene terephthalate comprising use of one or more (e.g. several) of the variants.

In some aspects the invention relates to a method of modifying polyester/cotton blend fabric comprising use of one or more of the cutinase and cellulase.

In some aspects the invention relates to a method for reducing the pilling propensity of fabrics comprising or consisting of polyester comprising use of one or more (e.g. several) of the variants. The improvement of pilling resistance may be determined by using the Martindale pilling tester (Swiss standard SN 198525) as described in the paragraph "Material and methods" infra.

The present invention is further described by the following examples that should not be construed as limiting the scope of the invention.

Materials and Methods

Unless otherwise indicated the materials are of reagent grade.

TABLE 1

Alterations in variants corresponding to amino acid position in SEQ ID NO: 2.

| Cutinase | ALTERATIONS |
|---|---|
| SEQ ID NO: 2 | — |
| 0004 | N79A |
| 0012 | A161L |
| 0016 | V115I |
| 0018 | A43C + I55C |
| 0022 | Q1* + L2* |
| 0035 | R181P + G182* |
| 0050 | I5V |
| 0077 | A43C + I55C + N79A |
| 0145 | I5V + A43C + I55C + N79A + V115I + R181P + G182* |
| 0179 | I5V + A43C + I55C + N79A + V115I |
| 0181 | Q1* + L2* + A43C + I55C + N79A + V115I + R181P + G182* |
| 0183 | Q1* + L2* + I5V + A43C + I55C + N79A + V115I + R181P + G182* |
| 0185 | A161L + R181P + G182* |
| 0186 | V115I + R181P + G182* |

Example 1: Cloning and Expression

Variants were generation by Site-directed mutagenesis using a forward primer containing the mutation. The PCR reaction mix contained 50 ng Template DNA; 10 pmol Mutagenic primer; 300 umol dNTP's; 1× of a 5×HF Phusion buffer; 0.5 mM MgCl2; 1 unit Phusion polymerase; and up to 25 uL MilliQ water. The PCR Cycle was run at 98° C./2:00 min; 18×(98° C./1:00 min, 62° C./1:00 min, 72° C./(2*length of plasmid in kb) min); 72° C./20:00 min; Hold at 4° C. Annealing temperature was changed according to Tm of mutagenic primer used. Digestion with DpnI was conducted with 0.5 uL DpnI enzyme added directly to the PCR reaction mix at 37° C. for 6 hours in the PCR machine.

5.0 uL of the reaction mix was directly transformed into chemically competent E. coli DH5α cells. 2-6 colonies were inoculated for plasmid isolation and the plasmid DNA sequence were confirmed for the incorporation of the desired mutation.

The confirmed plasmid DNA with the desired mutation was then transformed in Aspergillus oryzae and colonies obtained were screened for protein expression in small scale (2 mL in 24-well plates).

Small Scale Expression:

Spore suspension (0.2 g Agar (RM026, HiMedia); 0.05 g Tween20 (P9416, Sigma); and water to 100 mL was autoclaved and dispensed into 1 mL Nunc tubes).

YPM media (10 g Yeast extract (RM027, HiMedia); 20 g Peptone—(RM001, HiMedia); and water up to 1000 mL; Maltose (RM3050, HiMedia) from a 20% stock solution was added after autoclaving to a final concentration of 2%).

Spores from transformed colonies were transferred from the agar plate using an inoculation loop and spore suspension and inoculated in 2 mL YPM media in 12-well or 24-well culture plates. The plates were incubated at 34° C. without shaking under humid conditions for 3 days. The layer of mycelia formed on the surface of the media was removed and the culture media was analysed in SDS-PAGE and activity assay.

Aliquots of 40 uL were mixed with 10 uL SDS loading dye, heated at 100° C. for 10 minutes and loaded onto a 12% agarose gel and subsequently stained with Coomassie brilliant blue. Colonies with the best expression was streaked on COVE-N agar slants for shake-flask fermentation.

Shake-Flask Fermentation:

G2-Gly media (18 g Yeast Extract (RM027, HiMedia); 24.0 g Glycerol (87%, 10409405001730, Merck); 1.0 mL Dowfax 63N10 (Novozymes); and up to 1000 mL ion exchanged water).

MDU-2BP media (45.0 g Maltose (RM3050, HiMedia); 1.0 g Magnesium sulfate (61777005001730, Merck); 1.0 g Sodium chloride (1.93206.0521, Merck); 2.0 g Potassium sulfate (61777405001730, Merck); 12.0 g Potassium dihydrogen phosphate (1.93205.0521, Merck); 7.0 g Yeast Extract (RM027, HiMedia); 0.1 mL Dowfax 63N10 (Novozymes); 0.5 mL AMG Spormetal (KU6) (see below); and up to 1000 mL ion exchanged water).

AMG Spormetal (KU6) (6.8 g Zinc Chloride (61752905001046, Merck); 2.5 g Copper Sulfate (61775905001730, Merck); 0.13 g Nickel Chloride anhydrous (8067220100, Merck); 13.9 g Iron Sulfate (61751005001730, Merck); 8.45 g Manganese Sulfate (61754805001730, Merck); 3 g Citric acid (60024205001730, Merck); and up to 1000 mL ion exchanged water)

Approximately 5 mL of G2-Gly media in baffled flasks (200 mL media in 500 mL flasks) was poured into sporulated slants of the given variant. The spores were scraped out of the slants using an inoculation loop and re-suspended in the media, which was poured back into the flasks with the rest of the media. The flasks were covered with a layer of thick Mira-like cloth and paper and incubated at 34° C. for 24 hours at 180 rpm. After overnight growth, 2-5 mL of the G2-Gly culture was inoculated in 300 mL MDU-2BP media in 1 L baffled flasks. 50% urea was added to the autoclaved MDU-2BP media to a final concentration of 0.5% prior to inoculation. The flasks were incubated at 34° C. at 180 rpm for 72 hours. After 72 hours of growth, the supernatants were analyzed on 12% SDS-PAGE for expression. Once the SDS-PAGE showed expression of the desired protein, the fermentation broth was handed over for purification.

Example 2: Purification

The fermentation broth was filtered on a Buchner funnel (145 mm) fitted with a glass fibre filter sandwich. The filter sandwich consists of GF D/A/C/B and F filter, with filter D being on the top and filter F on the base of the Buchner funnel. The broth was subsequently passed through a 0.2 um hollow fibre filter fixed on a GE QuixStand® machine at a trans-membrane pressure maintained at 5 psi.

The sterile filtered broth was loaded onto a first column with a mixed mode resin HEA-HyperCel® (HEA is hexylamine). The resin was packed in a glass column (Kron lab) having a column diameter of 15 mm and a bed height of 200 mm. The purification process was automated using BioRad Duoflow pathfinder20® carried out in sequential steps as outlined below. All volumes, except the sample volume, were 8-10× column volumes.

| | |
|---|---|
| Chromatography/Resin | HEA HyperCel |
| Equilibration buffer | 100 mM Bicarbonate pH 10 |
| Sample | Sample + 100 mM NaCl |
| Unbound Wash 1 | 100 mM Bicarbonate pH 10 |
| Unbound Wash 2 | 50 mM Na acetate, pH 4.5 + 300 mM NaCl |
| Elution buffer | Na acetate 50 mM, pH 4.5 |
| Elution mode | Linear gradient |

Eluted fractions from the first column were pooled and the conductivity adjusted to 4 mS/cm by diluting it with Sodium acetate buffer, 50 mM, pH4.5 before loading onto a second column with a cation exchange resin UnoS® packed in a glass column (Kron lab) having a column diameter of 15 mm and a bed height of 200 mm. The purification process was automated using BioRad Duoflow pathfinder20® carried out in sequential steps as outlined below. All volumes, except the sample volume, are 8-10× column volumes.

| | |
|---|---|
| Chromatography/Resin | UNO S (Cation exchange resin) |
| Equilibration buffer | 50 mM Na acetate pH 4.5 |
| Sample | Sample with Na acetate pH 4.5 (conductivity less than 4 mS) |
| Unbound Wash | 50 mM Na acetate pH 4.5 |
| Elution buffer | Na acetate 50 mM, pH 4.5 + 1M NaCl |
| Elution mode | Step gradient |

Eluted fractions were pooled, resolved on SDS-PAGE for documentation, measured at $A_{280}$, packed and delivered.

Lame Scale Purification

The culture broth was centrifuged (20000×g, 20 min) and the supernatant was carefully decanted from the precipitate and filtered through a Nalgene 0.2 um filtration unit.

A 5M NaCl solution was added to the 0.2 um filtrate to a final concentration of 1M NaCl. The mixture was applied to a Decylamine-agarose column (from Upfront Chromatography) equilibrated in 40 mM $H_3BO_3$/NaOH, 1M NaCl, pH 9.0 and subsequently washed with 5× column volumes equilibration buffer and was step eluted with a mixture of 70% (50 mM $H_3BO_3$/NaOH, pH 9.0) and 30% Isopropanol.

The eluted peak from the Decylamine agarose step was applied to a SP-sepharose FF column (from GE Healthcare) equilibrated in 20 mM Acetic acid/NaOH, pH5.0. After washing the column extensively with the equilibration buffer, the cutinase was eluted with a linear gradient between the equilibration buffer and 20 mM Acetic acid/NaOH, 1.0M NaCl, pH 5.0 over 3× column volumes. The major peak from the SP-sepharose FF column containing the Cutinase was analyzed by SDS-PAGE and fractions, where only one band was seen on the coomassie stained SDS-PAGE gel, were pooled as the purified product.

Example 3: Cutinase Activity

For calculation of the residual activity of the parent and variant enzymes hydrolytic activity towards BETEB substrate (12.5 mg/mL BETEB; 0.1% Triton X-100, $H_2O$) was determined at two temperatures: 85° C. was considered as 100% activity and 90° C. was considered to show reduced activity.

For each test temperature (two controls (a "substrate blank" and an "enzyme blank") were included and tested under similar conditions as the enzyme sample. The enzyme sample was made by mixing 25 uL Culture supernatant from example 1 (sub) or Purified enzyme from example 2 (pur), 100 uL substrate up to 1 mL with a 40 mM Britton-Robinson Buffer pH 7.0 (Briton Robinson Buffer is an equimolar mixture of Boric acid, ortho-phosphoric acid and acetic acid. pH was adjusted using a 5× molar solution of NaOH). The "substrate blank" contained 100 uL substrate and up to 1 mL with a 40 mM Britton-Robinson Buffer pH 7.0. The "enzyme blank" contained 25 uL culture supernatant, 100 uL 0.1% Triton X-100 and up to 1 mL with a 40 mM Britton-Robinson Buffer pH 7.0. After incubation at 85° C. or 90° C. for 20 minutes at 1000 rpm the reactions were stopped immediately by placing the samples on ice for 1 to 5 minutes. They were subsequently centrifuged at 13000 rpm for 1 minute and absorbance at 254 nm of the supernatant was measured.

The improved residual activity of a variant as compared with the parent enzyme is expressed as a Relative % RA higher than 100. Calculation of Relative % RA was conducted according to the following: Relative % RA=(Variant % RA)/(SEQ ID NO: 2% RA)*100

TABLE 2

Residual activity (RA) of cutinase variants relative to SEQ ID NO: 2

| Cutinase | Relative % RA (sup) | Variant % RA (sup) | SEQ ID NO: 2% RA (sup) | Relative % RA (pur) | Variant % RA (pur) | SEQ ID NO: 2% RA (pur) |
|---|---|---|---|---|---|---|
| 0050 | 120 | 71 | 59 | 124 | 36 | 29 |
| 0018 | 300 | 66 | 22 | 163 | 62 | 38 |
| 0004 | 171 | 94 | 55 | 107 | 60 | 56 |
| 0016 | 164 | 36 | 22 | 74 | 28 | 38 |
| 0012 | 138 | 76 | 55 | 171 | 65 | 38 |
| 0035 | 206 | 64 | 31 | 86 | 25 | 29 |
| 0186 | 64 | 36 | 56 | 527 | 58 | 11 |
| 0185 | 200 | 84 | 42 | 1256 | 113 | 9 |
| 0183 | 289 | 162 | 56 | 773 | 85 | 11 |
| 0181 | 279 | 156 | 56 | 909 | 100 | 11 |
| 0179 | 448 | 121 | 27 | 584 | 111 | 19 |
| 0077 | 261 | 146 | 56 | 755 | 83 | 11 |
| 0145 | 525 | 126 | 24 | 204 | 116 | 57 |
| 0022 | 107 | 60 | 56 | 273 | 30 | 11 |

Example 4: Biopolishing with Cutinase in Laundry-O-Meter

Biopolishing with cutinase was carried out in a SDL-Atlas LP2 Launder-O-Meter (LOM) both in small scale (SSLOM) and full scale (FSLOM).

The fabric was cut into rectangular pieces/swatches of 5×10 cm about 1 g for SSLOM and 14×14 cm about 4-5 g for FSLOM. The fabric was side-locked by sewing. The pieces were conditioned at 65%+/−5% relative humidity and 20° C.+/−1° C. for 24 hours before they were numbered, weighted by an analytical balance (for samples below 100 g) or a precision balance (for samples over 100 g) and recorded.

One conditioned piece was placed in each beaker together with 10 small acid proof steel balls (M6M-SR-A4-80) providing mechanical aid. Buffer (Britton-Robinson Buffer, pH=8) and enzyme solutions were added as indicated in the tables based on the calculation of actual fabric weights, with a liquid to fabric v/w ratio of 10:1. At time 0 hour OD absorbance at 254 nm and the initial pH of solution were measured.

Each beaker was fitted with a lid lined with 2 neoprin gaskets and close tightly with the metal clamping device. The beakers were loaded into the LOM preheated to 70° C. Metal racks were used to accommodate and secure 5 beakers, in the vertical position, in each of the 4 drum positions. The LOM lid was closed and washing was conducted.

After 2 hours the fabrics were transferred to an inactivation solution (2 g/L sodium carbonate) at 95° C. for 10 minutes and subsequently rinsed twice in 1 L hot water followed by twice in 1 L cold water. The fabrics were tumble-dried (AEG, LAVATHERM 37700, Germany) for 1 hour after which they were conditioned as described above prior to evaluation.

The treating bath from each beaker was centrifuged at 13000 rpm for 1 minute and pH and OD absorbance at 254 nm were determined. Pilling note and weight loss of the fabric was evaluated.

The enzyme protein was measured with BCA™ Protein Assay Kit (product number 23225, commercial available from Thermo Fisher Scientific Inc.) according to the product manual.

OD Absorbance and pH Measurement

Cutinase activity was investigated by hydrolysis of PET or BETEB in eppendorf tubes. The hydrolysis products are terephthalate and its esters which have characteristic absorbance peaks around 254 nm (UV). The OD absorbance at 254 nm ($OD_{254}$) reflects the hydrolytic activity of the enzymes towards polyesters. Increase enzyme activity towards PET or BETEB result in an increase in $OD_{254}$. $OD_{254}$ is read in SpectraMax M2 Microplate Reader (Molecular Devices, LLC.). If the absorbance is beyond the effective range of the Reader of 1.5, the solution will be diluted. Dilution×15 means the solution has been diluted by 15 times.

The hydrolysis product terephthalate is acidic and will decrease pH of the solution. Accordingly the enzyme activity may be followed by measuring the change in pH before and after the reaction.

Pilling Note Test

Swatches including treated and untreated which had been pre-conditioned in norm climate (65% humidity, 20° C.) for at least 24 hours were tested for the pilling notes with Nu-Martindale Tester (James H. Heal Co. Ltd, England), with untreated fabrics of the same type as the abraded fabrics. A standard pilling test (Swiss Norm (SN) 198525) was carried out after 2000 Revolutions by marking from 1-5, with the meaning defined as below, where 1 shows poor anti-pilling and 5 shows excellent anti-pilling property. Thus the higher the Martindale pilling notes score the more effective the biopolishing treatment.

Note 5: No pilling

Note 4: Slight Pilling

Note 3: Moderate Pilling

Note 2: Distinct Pilling

Note 1: Heavy Pilling

1/2, 1/4 notes are allowed

Three separate readings were carried out by different persons for each sample, and the average of the three readings was adopted as the final result of pilling notes.

TABLE 3

Bioblasting of 100% stable PET woven in SSLOM[1]

| Cutinase | Conc.[2] (mg/g) | pH change | OD$_{254nm}$ change (5x dilution) | Pilling note[3] |
|---|---|---|---|---|
| — | 0 | 0.04 | 0.165 | 2.5 |
| 0004 | 1.4 | 0.36 | 2.291 | 3.1 |
| 0012 | 1.4 | 0.17 | 2.260 | 3.4 |
| 0016 | 1.4 | 0.64 | 2.470 | 3.4 |
| 0018 | 1.4 | 0.28 | 2.290 | 3.0 |
| SEQ ID NO: 2 | 1.4 | 0.09 | 1.761 | 3.0 |
| 0004 | 0.7 | 0.19 | 1.736 | 3.1 |
| 0012 | 0.7 | 0.16 | 2.127 | 3.4 |
| 0016 | 0.7 | 0.19 | 2.270 | 3.3 |
| 0018 | 0.7 | 0.15 | 1.8660 | 3.0 |
| SEQ ID NO: 2 | 0.7 | 0.13 | 1.4430 | 3.1 |
| — | 0 | 0.07 | 0.2043 | 2.8 |
| 0004 | 0.2 | 0.05 | 0.8499 | 3.0 |
| 0012 | 0.2 | −0.08 | 1.0084 | 2.6 |
| 0016 | 0.2 | 0.06 | 1.0860 | 3.0 |
| 0018 | 0.2 | −0.05 | 1.1016 | 2.9 |
| 0035 | 0.2 | 0.03 | 1.4519 | 2.9 |
| 0050 | 0.2 | 0.02 | 0.8666 | 3.0 |
| SEQ ID NO: 2 | 0.2 | 0.04 | 0.0730 | 2.9 |
| 0035 | 0.7 | 0.38 | 2.4047 | 3.4 |
| 0050 | 0.7 | 0.18 | 1.6238 | 2.9 |
| SEQ ID NO: 2 | 0.7 | 0.13 | 1.4428 | 2.8 |
| — | 0 | −0.22 | 0.2450 | 2.6 |
| 0035 | 1.4 | 0.08 | 1.5245 | 2.9 |
| 0050 | 1.4 | 0.07 | 1.5734 | 3.4 |
| SEQ ID NO: 2 | 1.4 | 0.09 | 1.8961 | 3.0 |
| Variant No: | | | | |
| — | 0 | −0.22 | 0.2450 | 2.6 |
| SEQ ID NO: 2 | 0.2 | 0.04 | 0.0730 | 2.9 |
| 0022 | 0.2 | 0.98 | 1.2565 | 3.1 |
| SEQ ID NO: 2 | 0.7 | 0.13 | 1.4428 | 2.8 |
| 0022 | 0.7 | 0.81 | 1.8400 | 2.8 |
| SEQ ID NO: 2 | 1.4 | 0.09 | 1.8961 | 3.0 |
| 0022 | 1.4 | 1.26 | 2.4121 | 3.4 |

[1]SSLOM was conducted with 100% stable PET woven (cationic dyable, CHN-2011-00461) at 70° C., pH 8.0.
[2]Concentration is indicated as mg of enzyme protein per g of fabric.
[3]Pilling note variation is about 0.2.

TABLE 4

Bioblasting of 100% stable PET woven in SSLOM[1]

| Cutinase | Conc.[2] (mg/g) | pH change | OD$_{254nm}$ change (5x dilution) | Pilling note[3] |
|---|---|---|---|---|
| — | 0.0 | 0.04 | 0.1650 | 2.5 |
| 0186 | 0.2 | 0.72 | 1.4102 | 2.9 |
| | 0.7 | 1.23 | 2.3147 | 3.6 |
| | 1.4 | 2.01 | 2.4478 | 3.6 |
| 0185 | 0.2 | 0.81 | 1.3320 | 2.9 |
| | 0.7 | 1.34 | 2.0554 | 3.4 |
| | 1.4 | 1.435 | 2.2885 | 2.9 |
| 0183 | 0.2 | 0.69 | 1.3617 | 3.0 |
| | 0.7 | 0.67 | 2.0704 | 3.6 |
| | 1.4 | 1.645 | 2.1703 | 3.8 |
| 0181 | 0.2 | 0.77 | 1.2701 | 2.8 |
| | 0.7 | 1.11 | 2.1750 | 3.8 |
| | 1.4 | 1.935 | 2.3606 | 3.8 |
| 0179 | 0.2 | 0.76 | 1.4356 | 2.6 |
| | 0.7 | 1.44 | 1.8637 | 3.5 |
| | 1.4 | 1.35 | 2.2318 | 3.8 |
| 0077 | 0.2 | 0.72 | 1.2547 | 2.6 |
| | 0.7 | 1.23 | 2.2480 | 3.4 |
| | 1.4 | 1.625 | 2.2608 | 3.7 |
| 0145 | 0.2 | 0.84 | 1.3100 | 2.8 |
| | 0.7 | 0.70 | 1.5883 | 2.8 |
| | 1.4 | 1.58 | 1.4930 | 2.8 |
| 0022 | 0.2 | 0.91 | 1.5045 | 2.9 |
| | 0.7 | 0.81 | 1.8400 | 2.8 |
| | 1.4 | 1.955 | 2.2885 | 3.5 |
| SEQ ID NO: 2 | 0.2 | 0.76 | 1.3600 | 2.9 |
| | 0.7 | 0.13 | 1.4428 | 2.8 |
| | 1.4 | 2.10 | 2.5033 | 3.5 |

[1]SSLOM was conducted with 100% stable PET woven (cationic dyable, CHN-2011-00461) at 70° C., pH 8.0.
[2]Concentration is indicated as mg of enzyme protein per g of fabric.
[3]Pilling note variation is about 0.2.

TABLE 5

Bioblasting of 100% stable PET woven in FSLOM[1]

| 0022 | Pilling note (2000R) | | pH change | | OD$_{254mn}$ change (5x dilution) | |
|---|---|---|---|---|---|---|
| 0 | 0.1 | 2.5 | 0.1 | 0.06 | 0.17 | 0.02 | 0.2328 |
| 0.1 | 0.1 | 3.5 | 0.3 | 0.04 | 0.67 | 0.03 | 1.3695 |
| 0.2 | 0.1 | 3.4 | 0.1 | 0.06 | 1.12 | 0.02 | 2.0297 |
| 0.4 | 0.1 | 3.8 | 0.3 | 0.08 | 1.80 | 0.11 | 2.4020 |
| 0.6 | 0.1 | 4.0 | 0.1 | 0.08 | 2.25 | 0.08 | 2.5043 |
| 0.7 | 0.3 | 4.0 | 0.1 | 0.07 | 2.44 | 0.06 | 2.5578 |
| 1.4 | 0.1 | 4.2 | 0.2 | 0.10 | 2.88 | 0.08 | 2.6238 |

| 0012 | Pilling note (2000R) | | pH change | | OD$_{254mn}$ change (5x dilution) | |
|---|---|---|---|---|---|---|
| 0 | 0.3 | 2.3 | 0.3 | 0.07 | 0.16 | 0.07 | 0.2308 |
| 0.1 | 0.3 | 3.0 | 0.3 | 0.04 | 0.47 | 0.03 | 0.9927 |
| 0.2 | 0.3 | 3.3 | 0.3 | 0.03 | 0.78 | 0.02 | 1.4685 |
| 0.4 | 0.3 | 3.4 | 0.3 | 0.13 | 1.23 | 0.04 | 2.0940 |
| 0.6 | 0.3 | 3.4 | 0.3 | 0.20 | 1.66 | 0.16 | 2.3651 |
| 0.7 | 0.1 | 3.5 | 0.1 | 0.01 | 1.83 | 0.01 | 2.3742 |
| 1.4 | 0.1 | 3.8 | 0.1 | 0.05 | 2.35 | 0.07 | 2.5362 |

| 0016 | Pilling note (2000R) | | pH change | | OD$_{254mn}$ change (5x dilution) | |
|---|---|---|---|---|---|---|
| 0 | 0.3 | 2.3 | 0.3 | 0.01 | 0.07 | 0.01 | 0.1567 |
| 0.1 | 0.3 | 2.7 | 0.4 | 0.02 | 0.55 | 0.05 | 1.1491 |
| 0.2 | 0.3 | 2.9 | 0.2 | 0.03 | 0.86 | 0.05 | 1.6099 |
| 0.4 | 0.3 | 3.1 | 0.2 | 0.01 | 1.41 | 0.01 | 2.2039 |
| 0.6 | 0.4 | 3.8 | 0.4 | 0.06 | 1.83 | 0.01 | 2.3927 |
| 0.7 | 0.1 | 3.8 | 0.1 | 0.22 | 1.98 | 0.16 | 2.4396 |
| 1.4 | 0.2 | 4.2 | 0.1 | 0.05 | 2.49 | 0.07 | 2.5499 |

| SEQ ID NO: 2 | Pilling note (2000R) | | pH change | | OD$_{254mn}$ change (5x dilution) | |
|---|---|---|---|---|---|---|
| 0 | 0.33 | 1.88 | 0.33 | 0 | 0.21 | 0 | 0.3572 |
| 0.1 | 0.13 | 2.04 | 0.13 | 0.02 | 0.44 | 0.02 | 0.7490 |
| 0.2 | 0.21 | 2.29 | 0.29 | 0.14 | 0.64 | 0.07 | 1.1305 |
| 0.4 | 0.13 | 2.50 | 0.13 | 0.10 | 0.91 | 0.05 | 1.7733 |
| 0.6 | 0.20 | 2.54 | 0.16 | 0.03 | 1.27 | 0.03 | 2.2171 |
| 0.7 | 0.21 | 2.42 | 0.17 | 0.06 | 1.33 | 0.04 | 2.2696 |
| 1.4 | 0.04 | 2.71 | 0.08 | 0.09 | 1.91 | 0.09 | 2.5438 |

TABLE 6

Bioblasting of 100% stable PET woven in FSLOM[1]

| Cutinase | Conc.[2] (mg/g) | pH change | OD$_{254nm}$ change (5x dilution) | Pilling note |
|---|---|---|---|---|
| 0186 | 0.0 | 0.24 | 0.2570 | 2.50 |
|  | 0.05 | 0.59 | 1.1203 | 3.56 |
|  | 0.1 | 0.71 | 1.6763 | 3.63 |
|  | 0.2 | 1.03 | 2.1400 | 3.63 |
|  | 0.4 | 1.28 | 2.4107 | 4.00 |
|  | 0.6 | 1.72 | 2.5565 | 4.00 |
| 0185 | 0.0 | 0.17 | 0.2519 | 2.88 |
|  | 0.05 | 0.73 | 1.1842 | 3.63 |
|  | 0.1 | 1.00 | 1.6380 | 3.75 |
|  | 0.2 | 1.37 | 2.1413 | 4.13 |
|  | 0.4 | 1.90 | 2.4378 | 4.38 |
|  | 0.6 | 2.61 | 2.5141 | 4.38 |
| 0183 | 0.0 | 0.18 | 0.2263 | 2.63 |
|  | 0.05 | 0.63 | 1.0902 | 3.56 |
|  | 0.1 | 0.84 | 1.6655 | 3.81 |
|  | 0.2 | 1.08 | 1.9802 | 3.81 |
|  | 0.4 | 1.31 | 2.2020 | 4.13 |
|  | 0.6 | 1.88 | 2.4693 | 4.00 |
| 0181 | 0.0 | 0.18 | 0.2263 | 2.88 |
|  | 0.05 | 0.57 | 1.0009 | 3.06 |
|  | 0.1 | 0.75 | 1.3348 | 3.31 |
|  | 0.2 | 1.10 | 1.9916 | 3.81 |
|  | 0.4 | 1.40 | 2.3028 | 3.50 |
|  | 0.6 | 1.83 | 2.4202 | 3.63 |
| 0179 | 0.0 | 0.24 | 0.2263 | 2.50 |
|  | 0.05 | 0.58 | 1.0902 | 3.38 |
|  | 0.1 | 0.72 | 1.6655 | 3.69 |
|  | 0.2 | 1.01 | 1.9802 | 3.75 |
|  | 0.4 | 0.48 | 2.2020 | 4.00 |
|  | 0.6 | 0.59 | 2.4693 | 3.50 |
| 0077 | 0.0 | 0.28 | 0.3321 | 2.25 |
|  | 0.05 | 0.61 | 1.0560 | 2.42 |
|  | 0.1 | 0.84 | 1.4819 | 2.79 |
|  | 0.2 | 1.23 | 2.0324 | 2.96 |
|  | 0.4 | 1.74 | 2.4135 | 3.58 |
|  | 0.6 | 2.18 | 2.4871 | 3.54 |
|  | 0.7 | 2.22 | 2.5304 | 3.75 |
| 0145 | 0.0 | 0.21 | 0.2209 | 2.25 |
|  | 0.1 | 0.76 | 1.2424 | 3.29 |
|  | 0.2 | 1.07 | 1.7571 | 3.42 |
|  | 0.4 | 1.47 | 2.2310 | 3.96 |
|  | 0.6 | 1.79 | 2.3507 | 3.94 |
|  | 0.7 | 2.05 | 2.4692 | 3.96 |
| 0022 | 0.0 | 0.17 | 0.2328 | 2.50 |
|  | 0.1 | 0.67 | 1.3695 | 3.46 |
|  | 0.2 | 1.12 | 2.0297 | 3.42 |
|  | 0.4 | 1.80 | 2.4020 | 3.75 |
|  | 0.6 | 2.25 | 2.5043 | 3.96 |
|  | 0.7 | 2.44 | 2.5578 | 3.96 |
|  | 1.4 | 2.88 | 2.6238 | 4.17 |
| SEQ ID NO: 2 | 0.0 | 0.28 | 0.2096 | 2.63 |
|  | 0.05 | 0.37 | 1.1149 | 2.63 |
|  | 0.1 | 0.45 | 1.4730 | 2.69 |
|  | 0.2 | 0.61 | 1.6830 | 2.63 |
|  | 0.4 | 0.76 | 2.3857 | 2.63 |
|  | 0.6 | 0.95 | 2.5069 | 2.75 |

[1]FSLOM was conducted with 100% stable PET woven (cationic dyable, CHN-2011-00461) at 70° C., pH 8.0.
[2]Concentration is indicated as mg of enzyme protein per g of fabric.
[3]Pilling note variation is about 0.2.

TABLE 7

Bioblasting of various PET-Cotton blended fabrics in FSLOM[1]

| Fabric | Conc.[2] (mg/g) | 0186 | 0185 | 0181 | SEQ ID No: 2 |
|---|---|---|---|---|---|
| CHN-2012-00999 TC 65/35 Lacoste | 0.2 | 2.8 ± 0.2 | 2.8 ± 0.2 | — | 2.8 ± 0.2 |
|  | 0.4 | 2.9 ± 0.1 | 2.9 ± 0.1 | — | 2.4 ± 0.1 |
| CHN-2012-01237 TC 65/35 knit | 0.2 | — | 2.5 ± 0.2 | 2.5 | 2.4 ± 0.1 |
|  | 0.4 | — | 2.8 ± 0.1 | 2.4 ± 0.1 | 2.6 ± 0.1 |
| CHN-2012-00922 TC 65/35 knit | 0.2 | 2.8 ± 0.1 | 3.1 ± 0.1 | 2.8 ± 0.1 | 2.8 ± 0.1 |
|  | 0.4 | 3.1 ± 0.1 | 3.5 ± 0.2 | 3.6 ± 0.1 | 3.4 ± 0.1 |
| CHN-2012-00733 TC 65/35 woven | 0.7 | 3.2 ± 0.2 | 3.1 ± 0.1 | 3.2 ± 0.2 | 3.0 |

[1]FSLOM was conducted with various PET-Cotton blended fabrics at 70° C., pH 8.0.
[2]Concentration is indicated as mg of enzyme protein per g of fabric.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A variant with cutinase activity of a parent cutinase, comprising an alteration at one or more positions corresponding to positions: 36, 37, 40, 78, 90, 114, 150, 196, 216, or 217 of SEQ ID NO: 2, wherein the alteration is a substitution for positions 40, 78, 90, 114, 150, 196 and 216, and a deletion for positions 36, 37 and 217, and wherein the variant has at least 80%, but less than 100% sequence identity to amino acids 36 to 229 of SEQ ID NO: 2.

2. The variant of claim 1, wherein the variant has at least 85% sequence identity to amino acids 36 to 229 of SEQ ID NO: 2.

3. The variant of claim 1, wherein the variant has at least 90% sequence identity to amino acids 36 to 229 of SEQ ID NO: 2.

4. The variant of claim 1, wherein the variant has at least 95% sequence identity to amino acids 36 to 229 of SEQ ID NO: 2.

5. The variant of claim 1, which comprises one or more alterations selected from the group consisting of Q36*, L37*, I40V, A78C, I90C, N114A, V150I, A196L, R216P and G217*.

6. The variant of claim 1, which comprises or consists of alterations selected from the group consisting of:
 a. I40V
 b. N114A
 c. V150I
 d. A196L
 e. Q36*+L37*
 f. A78C+I90C
 g. R216P+G217*
 h. A78C+I90C+N114A i. V150I+R216P+G217*
j. A196L+R216P+G217*
k. I40V+A78C+I90C+N114A+V150I
l. I40V+A78C+I90C+N114A+V150I+R216P+G217*
m. Q36*+L37*+A78C+I90C+N114A+V150I+R216P+G217*
n. Q36*+L37*+I40V+A78C+I90C+N114A+V150I+R216P+G217*.

7. The variant of claim 1, further comprising an N-terminal extension to the amino acid corresponding to amino acid 36 of SEQ ID NO: 2.

8. The variant of claim 7 wherein the N-terminal extension is selected from:

```
a. AAVDSNHTPAVPELVAR    (SEQ ID NO: 3)
b. AVDSNHTPAVPELVAR     (SEQ ID NO: 4)
c. VDSNHTPAVPELVAR      (SEQ ID NO: 5)
d. DSNHTPAVPELVAR       (SEQ ID NO: 6)
e. SNHTPAVPELVAR        (SEQ ID NO: 7)
f. NHTPAVPELVAR         (SEQ ID NO: 8)
g. HTPAVPELVAR          (SEQ ID NO: 9)
h. TPAVPELVAR           (SEQ ID NO: 10)
i. PAVPELVAR            (SEQ ID NO: 11)
j. AVPELVAR             (SEQ ID NO: 12)
k. VPELVAR              (SEQ ID NO: 13)
l. PELVAR               (SEQ ID NO: 14)
m. ELVAR                (SEQ ID NO: 15)
n. LVAR                 (SEQ ID NO: 16)
o. VAR
p. AR
q. R.
```

9. The variant of claim 1, which has an improved property relative to the parent, wherein the improved property is selected from the group consisting of specific activity, substrate binding, substrate cleavage, substrate specificity, thermostability, and decreased pilling propensity.

10. A composition comprising the variant of claim 1.

11. A polynucleotide encoding the variant of claim 1.

12. A nucleic acid construct comprising the polynucleotide of claim 11.

13. An expression vector comprising the polynucleotide of claim 11.

14. A host cell comprising the polynucleotide of claim 11.

15. A method of producing a cutinase variant, comprising:
   a. cultivating the host cell of claim 14 under conditions suitable for expression of the variant; and
   b. recovering the variant.

16. A method for obtaining a cutinase variant, comprising introducing into a parent cutinase an alteration at one or more positions corresponding to positions 36, 37, 40, 78, 90, 114, 150, 196, 216, or 217 of SEQ ID NO: 2, wherein the alteration is a substitution for positions 40, 78, 90, 114, 150, 196 and 216, and a deletion for positions 36, 37 and 217, and the variant has cutinase activity; and recovering the variant.

17. A method for modifying polyester, the method comprising treating the polyester with the variant of claim 1.

18. A method for hydrolyzing cyclic oligomers of poly (ethylene terephthalate), the method comprising treating the oligomers with the variant of claim 1.

19. A method for reducing the pilling propensity of fabric, wherein the fabric comprises or consists of polyester, the method comprising treating the fabric with the variant of claim 1.

* * * * *